US008637614B2

(12) United States Patent
Gorodisher et al.

(10) Patent No.: US 8,637,614 B2
(45) Date of Patent: *Jan. 28, 2014

(54) REACTIVE LIQUID MODIFIERS

(75) Inventors: Ilya Gorodisher, Stillwater, MN (US); Alphonsus V. Pocius, Maplewood, MN (US); Babu N. Gaddam, Woodbury, MN (US); Richard G. Hansen, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 133 days.

This patent is subject to a terminal disclaimer.

(21) Appl. No.: 13/055,192

(22) PCT Filed: Jul. 22, 2009

(86) PCT No.: PCT/US2009/051351
§ 371 (c)(1),
(2), (4) Date: Jan. 21, 2011

(87) PCT Pub. No.: WO2010/011714
PCT Pub. Date: Jan. 28, 2010

(65) Prior Publication Data
US 2011/0130518 A1    Jun. 2, 2011

Related U.S. Application Data

(60) Provisional application No. 61/082,862, filed on Jul. 23, 2008.

(51) Int. Cl.
| C08L 63/00 | (2006.01) |
| C08K 5/06 | (2006.01) |
| C08K 5/16 | (2006.01) |
| C08G 59/50 | (2006.01) |

(52) U.S. Cl.
USPC ......................................... 525/529; 525/526

(58) Field of Classification Search
USPC ........... 560/19, 27, 29, 37, 38, 41, 42, 45, 51, 560/55, 61; 525/525, 526, 529
See application file for complete search history.

(56) References Cited

U.S. PATENT DOCUMENTS

| 4,119,615 | A | | 10/1978 | Schulze |
| 4,263,366 | A | | 4/1981 | Lorenz et al. |
| 4,332,713 | A | | 6/1982 | Lehmann |
| 4,401,776 | A | | 8/1983 | Munk |
| 4,476,285 | A | | 10/1984 | Crabtree et al. |
| 4,778,851 | A | | 10/1988 | Henton et al. |
| 4,874,822 | A | * | 10/1989 | Rasmussen et al. ........... 525/279 |
| 4,906,772 | A | | 3/1990 | Chew et al. |
| 5,026,794 | A | | 6/1991 | Ho et al. |
| 5,290,624 | A | | 3/1994 | Bujard |
| 5,494,977 | A | | 2/1996 | Harano et al. |
| 5,629,380 | A | | 5/1997 | Baldwin et al. |
| 5,686,509 | A | | 11/1997 | Nakayama et al. |
| 6,180,693 | B1 | | 1/2001 | Tang et al. |
| 6,465,558 | B2 | | 10/2002 | Scheibelhoffer et al. |
| 6,554,936 | B1 | | 4/2003 | Metcalf et al. |
| 6,555,227 | B2 | | 4/2003 | Sprenger et al. |
| 6,664,318 | B1 | | 12/2003 | Bymark et al. |
| 8,491,749 | B2 | * | 7/2013 | Gorodisher et al. ........... 156/330 |
| 2004/0110856 | A1 | * | 6/2004 | Young et al. ....................... 522/6 |
| 2008/0121851 | A1 | | 5/2008 | Reinheimer |
| 2010/0294427 | A1 | | 11/2010 | Forster et al. |
| 2011/0039108 | A1 | | 2/2011 | Goeb et al. |
| 2011/0120646 | A1 | | 5/2011 | Gorodisher et al. |
| 2011/0126980 | A1 | | 6/2011 | Campbell et al. |
| 2011/0130518 | A1 | | 6/2011 | Gorodisher et al. |

FOREIGN PATENT DOCUMENTS

| EP | 230666 | 8/1987 |
| EP | 301720 | 2/1989 |
| EP | 336762 | 10/1989 |
| EP | 483974 | 5/1992 |
| EP | 0 593 936 | 4/1994 |
| EP | 847420 | 2/2000 |
| EP | 1125960 | 8/2001 |
| EP | 847410 | 11/2001 |
| EP | 1280842 | 11/2005 |
| EP | 1271043 | 9/2006 |
| GB | 2444364 | 6/2008 |
| JP | 6169879 | 4/1986 |
| JP | 05156225 | 6/1993 |
| JP | 11061072 | 3/1999 |
| JP | 2000-204232 | 7/2000 |
| JP | 2000-204233 | 7/2000 |
| JP | 2004-099786 | 4/2004 |
| JP | 2005272813 | 10/2005 |

(Continued)

OTHER PUBLICATIONS

Dean, K. et al., "Curing behavior of IPNs formed from model VERs and epoxy systems I amine cured epoxy", Polymer 42 (2001) p. 1345-1359.
Aikins, "Radiation-induced cationic polymerization of terpene epoxides", American Chemical Society, Division of Polymer Chemistry, Polymer Preprints, vol. 24, No. 260, (1984).
Andreopoulos, "Treated Polyethylene Fibres as Reinforcement for Epoxy Resins", Journal of Materials Science, vol. 1993, pp. 5002-5006.
ASTM C813-90 e1, "Standard Test Method for Hydrophobic Contamination on Glass by Contact Angle Measurement," 3 pages 1994.

(Continued)

Primary Examiner — Michael J Feely
(74) Attorney, Agent, or Firm — Dena M. Ehrich

(57) ABSTRACT

Epoxy reactive liquid modifiers include acrylate functionalized compounds, acrylamide functionalized compounds, oxalic amide functionalized compounds, actoacetoxy functionalized urethanes and acetoacetoxy functionalized polyalkenes. The reactive liquid modifiers are incorporated into epoxy resin compositions comprising a curable epoxy resin, an amine curing agent, and the reactive liquid modifier, wherein the reactive liquid modifier is polymerized to form at least one of an interpenetrating polymer network and a semi-interpenetrating polymer network with the curable epoxy resin.

3 Claims, 6 Drawing Sheets

(56) References Cited

FOREIGN PATENT DOCUMENTS

| | | |
|---|---|---|
| WO | WO 95/00597 | 1/1995 |
| WO | WO 99/67312 | 12/1999 |
| WO | WO 00/22024 | 4/2000 |
| WO | WO 01/77202 | 10/2001 |
| WO | WO 02/24792 | 3/2002 |
| WO | WO 02/062909 | 8/2002 |
| WO | WO 02/102909 | 12/2002 |
| WO | WO 03/078163 | 9/2003 |
| WO | WO 03/097756 | 11/2003 |
| WO | WO 2005/048866 | 6/2005 |
| WO | WO 2006/093949 | 9/2006 |
| WO | WO 2006/128722 | 12/2006 |
| WO | WO 2008/016889 | 2/2008 |
| WO | WO 2008/089410 | 7/2008 |
| WO | WO 2008/147614 | 12/2008 |
| WO | WO 2009/126862 | 10/2009 |

OTHER PUBLICATIONS

ASTM D 1002-05.
ASTM D 1876-08.
ASTM D 281-95 (Reapproved 2007) Standard Test Method for Oil Absorption of Pigments by Spatula Rub-out, 2 pages.
ASTM D 6386-99.
"Azo Compounds", Sigma-Aldrich, [online], [retrieved from the internet on Oct. 5, 2011], http://www.sigmaaldrich.com/materials-science/material-science-products.html?TablePage=20396479http://www.sigmaaldrich.com/materials-science/material-science-products.html?TablePage=20396479, 1 page.
"Coating Additives: Prevention of Crack Formation Using CoatForce® in Building Paints", Lapinus Fibres by, Technical Literature (2008).
Cooper, "Adhesive Properties of Terpene Cleaning Solvent Residues", Annual Technical Conference—ANTEC, Conference Proceedings, vol. 6, No. 233, (2005).
Clemens, Chem Rev., vol. 86, pp. 241 (1986).
Fakuda, "Synthesis of Macrocyclic Amides and Their Intermediate 2:1 and 3:2 Reaction Compounds from Diethyl Oxalate and Ethereal Oxygen-Containing Diamines", Bulletin of the Chemical Society of Japan, Chemical Society of Japan, vol. 69, No. 5, Jan. 1, 1996, pp. 1397-1401, (XP009138015).
Hansen, "Surface Tension by Pendant Drop," Journal of Colloid and Interface Science, vol. 141, No. 1, (Jan. 1991) p. 1-9.
Heilmann, "Acrylic-Functional Aminocarboxylic Acids and Derivatives as Components of Pressure-Sensitive Adhesives", J. Appl. Polym. Sci., vol. 24, 1979, pp. 1551-??.
Heilmann, "Chemistry of Alkenyl Azlactones IV. Preparation and Properties of Telechelic Acrylamides Derived from Amine-Terminated Oligomers", J. Polymer Sci.: Polymer Chem. Ed., vol. 22, 1984, pp. 3149-3160.
Hong, "Assimilation of Oil from Metal Surfaces by Epoxy Adhesives: XPS and ATR Analyses," Journal of Applied Polymer Science, vol. 55, 1995, pp. 437-449.
Janssen, "Bridging Gaps: New Mineral Fibres Offer a Variety of Coatings Performance Improvements", European Coatings Journal 1-2, pp. 30-33 (2006).
Liu, "Alkoxysilane Functionalized Polycaprolactone/polysiloxane Modififed Epoxy Resin Through Sol-gel Process", European Polymer Journal, vol. 44, No. 3, Dec. 23, 2007, pp. 940-951, (XP022519383).
Mark, Encyclopedia of Polymer Science and Engineering, 3rd Ed., Wiley-Interscience, New York, 2004, vol. 11, pp. 359.
Metal Bonding Structural Adhesive Performance Requirements, GM Worldwide Engineering Standards, Material Specification: Adhesives, Ballot Mar. 26, 2007, GMW15200.
"Organic Peroxides", Sigma Aldrich, [online], [retrieved from the internet on Oct. 5, 2011], http://www.sigmaaldrich.com/materials-science/material-science-products.html?TablePage=20396497, 2 pages.
Palamidessi, "Derivati Della Pirazina, Nota IX, Sulla 2,3-dicloropirazina", Farmaco, Societa Chimica Italiana, vol. 21, Jan. 1, 1966, pp. 799-804, (XP009138014).
Pocius, Adhesion and Adhesives Technology, $2^{nd}$ Ed., Hanser: Cincinnati, OH, pp. 186 and 201, (2002).
Polymer Chemistry, The Basic Concepts, Paul C. Hiemenz, Marcel Dekker, 1984.
Registry, RN 54735-63-6 XP002568424 abstract.
Samui, "Electroatractive Polymer Gels Based on Epoxy Resin", Smart Materials and Structures, vol. 16, 2007, pp. 237-242, (XP002568425).
Sigma Aldrich Catalog, (XP002568433).
"Solvent Cleaning", Surface Preparation Specifications and Practices, Edition SSPC 05-03, pp. 52-53 (2005).
Taylor, "The Synthesis of Vinyl Peptide Monomers", J. Polym. Sci. Polym. Lett. Ed., vol. 7, 1969, pp. 597-603.
van Krevelen, Properties of Polymers: Their Correlations with Chemical Structure: Their Numerical Estimation and Prediction from Additive Group Contributions, 4th Ed., 1990, Elsevier: Amsterdam, The Netherlands, pp. 220-225.
Wicks, "Blocked Isocyanates III: Part A, Mechanisms and Chemistry", Progress in Organic Coatings, vol. 36, 1999, pp. 148-172, (XP002598687).
Witzeman, J. Org. Chem., 56, 1713 (1991).
International Search Report, PCT/US2009/051351, 9 pages.

* cited by examiner

REACTIVE LIQUID MODIFIERS

CROSS REFERENCE TO RELATED APPLICATIONS

This application is a national stage filing under 35 U.S.C. 371 of PCT/US2009/051351, filed Jul. 22, 2009, which claims priority to U.S. Provisional Application No. 61/082,862, filed Jul. 23, 2008, the disclosure of which is incorporated by reference in its/their entirety herein.

FIELD OF THE INVENTION

The present invention relates to reactive liquid modifiers that may be used to enhance the performance of epoxy resins. The present invention also relates to methods of making and using the reactive liquid modifiers.

BACKGROUND

Epoxy resins are thermosetting epoxide polymers that undergo polymerization and cross-linking when exposed to curing agents, such as primary or secondary amines. Applications for epoxy resins are extensive and include general-use industrial applications, as well as high-performance applications in the automotive and aerospace industries.

The usefulness of epoxy resins in many engineering applications is often limited by their brittle nature. Several approaches that have been taken to enhance the toughness of epoxy resins include: chemical modification of the epoxy backbone to produce a more flexible structure; increasing the molecular weight of the epoxy resin; lowering the cross-linking density of the epoxy matrix; incorporation of a dispersed toughener phase in the cured polymer matrix; and, incorporation of inorganic fillers into the neat resin.

Despite the above efforts to enhance the toughness of epoxy resins, there is an ongoing need for additional ways to overcome the inherent brittleness of cured epoxy resins.

SUMMARY

In one embodiment, the invention provides a compound having the formula $$Y\text{—}[(O\text{—}(CO)\text{—}(CH_2)_5)_m\text{—}O\text{—}(CO)\text{—}(CH_2)_p\text{—}C(R^2)(R^3)\text{—}NH\text{—}(CO)\text{—}CH=CH_2]_n$$

wherein Y is a branched or linear alkyl chain having from about 1 to 10 carbon atoms or a heteroalkyl chain having from about 1 to 10 carbon atoms; each m is, independently, an integer value ranging from about 1 to 20; n is an integer value ranging from about 1 to 5; $R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having from about 4 to 12 carbon atoms; and each p is, independently, 0 or 1.

In another embodiment, the invention provides a compound having the formula

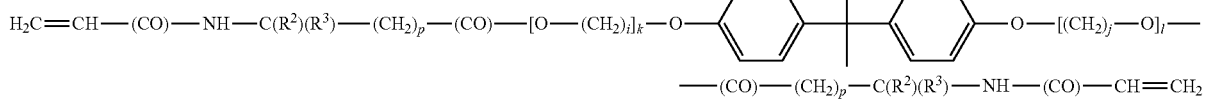
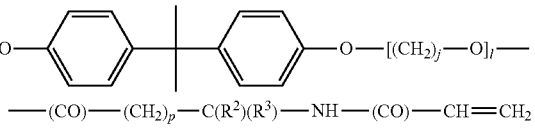

OR

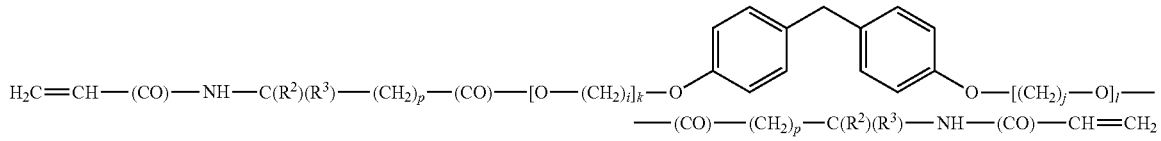
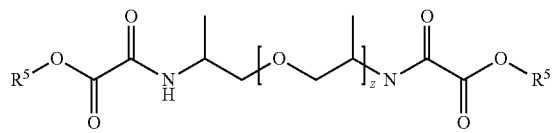

wherein i and j are each, independently, integer values of at least 1 whose combined sum ranges from about 2 to 10; k and l are each, independently, integer values of at least 1 whose combined sum ranges from about 2 to 120; $R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having from about 4 to 12 carbon atoms; and each p is, independently, 0 or 1.

In a further embodiment, the invention provides a compound having the formula

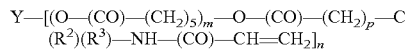

wherein z is an integer value ranging from about 1 to 75; and $R^5$ is an alkyl group having from about 1 to four carbon atoms, a cycloalkyl group having from about 3 to 12 carbon atoms, or an aromatic group having from about 6 to 12 carbon atoms.

In yet a further embodiment, the invention provides a compound having the formula

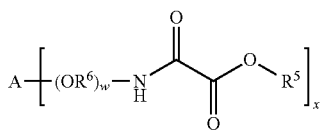

wherein A is a branched or linear alkyl chain having from about 1 to 10 carbon atoms; $R^6$ is a branched or linear alkyl chain having from about 1 to 5 carbon atoms; each w is, independently, an integer value ranging from about 1 to 130; x is an integer value ranging from about 1 to 40; and $R^5$ is an alkyl group having from about 1 to 4 carbon atoms, a cycloalkyl group having from about 3 to 12 carbon atoms, or an aromatic group having from about 6 to 12 carbon atoms.

In another embodiment, the invention provides an epoxy resin composition comprising a curable epoxy resin, an amine curing agent, and a reactive liquid modifier comprising a compound from above, wherein the compound is polymerized to form at least one of an interpenetrating polymer network and a semi-interpenetrating polymer network with the curable epoxy resin.

In yet another embodiment, the invention provides an epoxy resin composition comprising a curable epoxy resin, an amine curing agent, and a reactive liquid modifier comprising an oligourethane polyol capped with one or more acetoacetoxy functional compounds, wherein the reactive liquid modifier is polymerized to form at least one of an interpenetrating polymer network and a semi-interpenetrating polymer network with the curable epoxy resin.

In further embodiment, the invention provides an epoxy resin composition comprising a curable epoxy resin, an amine curing agent, and a reactive liquid modifier having the formula

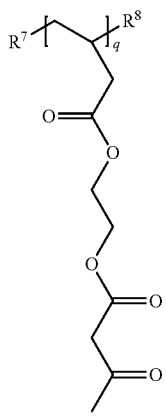

wherein q is an integer or a non-integer number ranging from about 1 to about 10; $R^7$ is H or an initiator fragment from a thermally decomposing initiator; and $R^8$ is H, an initiator fragment from a thermally decomposing initiator, or a thioester having the formula

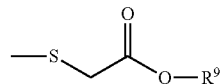

where $R^9$ is a $C_1$-$C_{12}$ linear alkyl, a $C_1$-$C_{12}$ branched alkyl or a $C_1$-$C_{12}$ cyclic alkyl, and wherein the reactive liquid modifier is polymerized to form at least one of an interpenetrating polymer network and a semi-interpenetrating polymer network with the curable epoxy resin.

In yet a further embodiment, the invention provides an epoxy resin composition comprising a curable epoxy resin, an amine curing agent, and a reactive liquid modifier having the formula $$Y-[(O-(CO)-(CH_2)_5)_g-O-(CO)-C(R^1)=CH_2]_h$$

wherein Y is a branched or linear alkyl chain having from about 1 to 10 carbon atoms or a heteroalkyl chain having from about 1 to 10 carbon atoms; each $R_1$ is, independently, H or a $C_1$-$C_4$ alkyl; each g is, independently, an integer value ranging from about 1 to 35; and h is an integer value ranging from about 1 to 22, and wherein the reactive liquid modifier is polymerized to form at least one of an interpenetrating polymer network and a semi-interpenetrating polymer network with the curable epoxy resin.

In another embodiment, the invention provides an epoxy resin composition comprising a curable epoxy resin, an amine curing agent, and a reactive liquid modifier having the formula

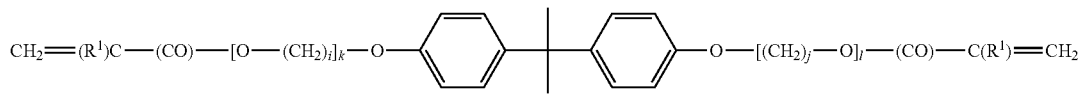

OR

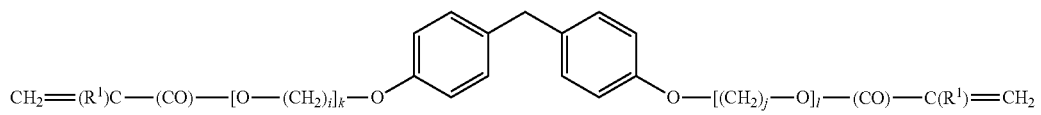

wherein each $R^1$ is, independently, H or a $C_1$-$C_4$ alkyl; i and j are each, independently, integer values ranging from 1 to 10; and k and l are each, independently, integer values of at least 1 whose combined sum ranges from about 2 to 135, and wherein the reactive liquid modifier is polymerized to form at least one of an interpenetrating polymer network and a semi-interpenetrating polymer network with the curable epoxy resin.

Other features and aspects of the invention will become apparent by consideration of the detailed description and accompanying drawings.

DETAILED DESCRIPTION

Figure 1:
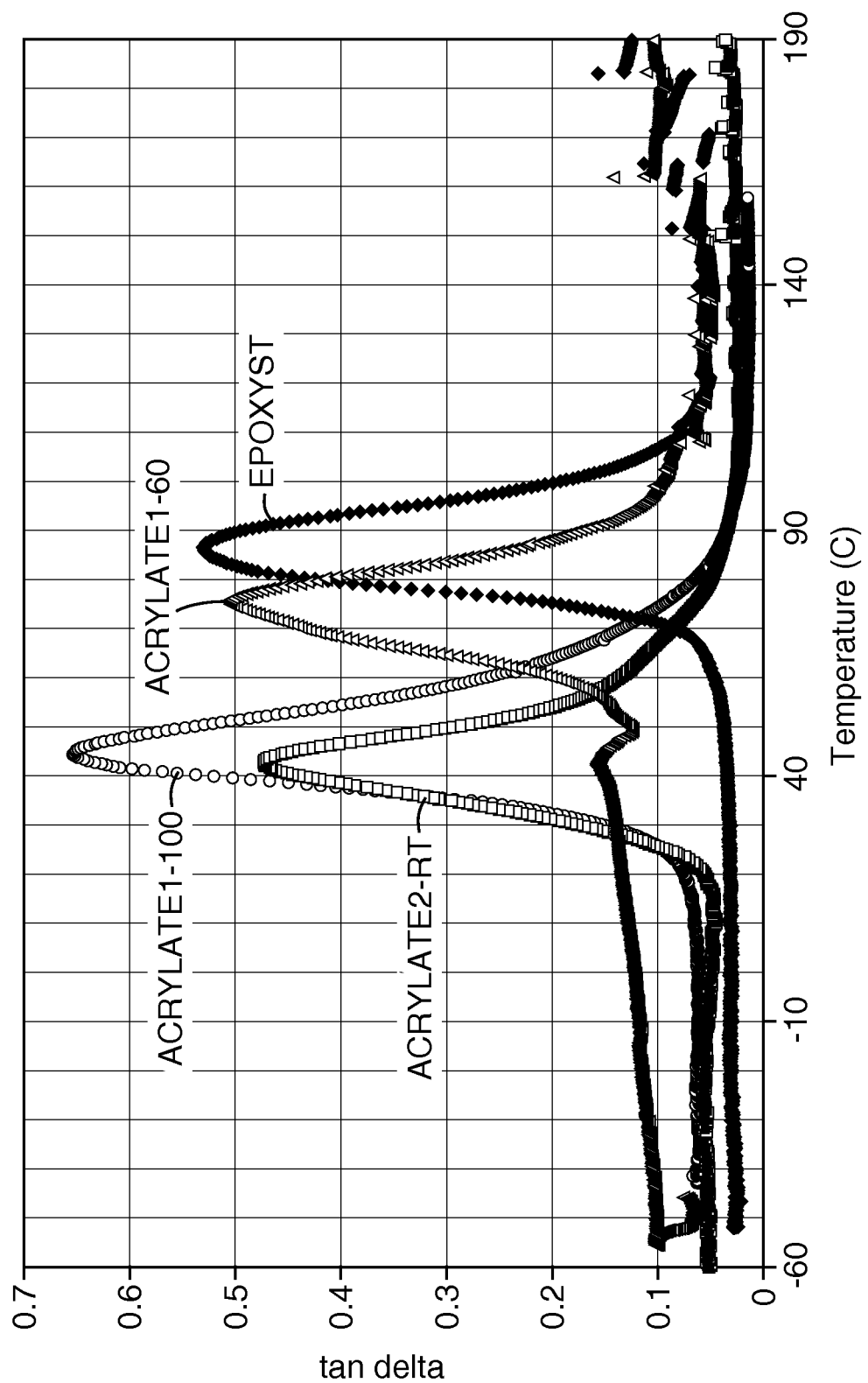
FIG. 1 is a DMA plot of tangent delta versus temperature for various acrylate-epoxy adhesives described in Example 1.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Reactive Liquid Modifiers

The present invention relates to reactive liquid modifiers for use in epoxy resin compositions. Without wishing to be bound by theory, it is believed that the reactive liquid modifiers polymerize to form an interpenetrating polymer network and/or semi-interpenetrating polymer network (referred to collectively as "IPNs") with the epoxy resins. As used herein, interpenetrating polymer network refers to an intimate combination of two polymers both in network form, at least one of which is synthesized and/or cross-linked in the immediate presence of the other. Semi-interpenetrating polymer network refers to a combination of two polymers, one cross-linked and one linear, at least one of which is synthesized and/or cross-linked in the immediate presence of the other. The IPNs are believed to enhance the performance of the epoxy resin compositions.

Suitable reactive liquid modifiers have a molecular weight less than about 4,000 g/mole. Reactive liquid modifiers having larger molecular weights are typically incompatible with the epoxy resins, resulting in phase separation and diminished adhesive strength. In some embodiments of the present invention, the reactive liquid modifier has a molecular weight of less than about 4,000 g/mole, in some embodiments a molecular weight of less than about 3,500 g/mole, and in some embodiments a molecular weight of less than about 2,000 g/mole. In some embodiments of the present invention, the reactive liquid modifier has a molecular weight of at least about 100 g/mole, in some embodiments a molecular weight of at least about 200 g/mole, and in some embodiments a molecular weight of at least about 500 g/mole.

In some embodiments of the present invention, the reactive liquid modifier has a molecular weight of from about 100 g/mole to about 4,000 g/mol. In other embodiments, the reactive liquid modifier has a molecular weight of from about 200 g/mole to about 3,500 g/mole. In further embodiments, the reactive liquid modifier has a molecular weight of from about 500 g/mole to about 2,000 g/mole.

The reactive liquid modifiers of the present invention may be polymerized by chain-initiated homopolymerization or by condensation reactions with amine curing agents to form IPNs. Reactive liquid modifiers that undergo chain initiated homopolymerization include acrylate functionalized compounds and acrylamide functionalized compounds. Reactive liquid modifiers that undergo condensation reactions include oxalic amide functionalized compounds, acetoacetoxy functionalized urethanes, and acetoacetoxy functionalized polyalkenes.

Acrylate Functionalized Compounds

Acrylate functionalized compounds may be mono-, di- or poly-functionalized compounds. Suitable acrylate functionalized compounds include caprolactone derivatives having general formula (IV):

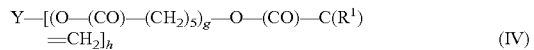
$$Y\text{---}[(O\text{---}(CO)\text{---}(CH_2)_5)_g\text{---}O\text{---}(CO)\text{---}C(R^1)=CH_2]_h \quad (IV)$$

where Y represents a branched or linear alkyl chain having from about 1 to 10 carbon atoms (e.g., methyl, ethyl, propyl, isopropyl, n-butyl, t-butyl, etc.) or a heteroalkyl chain having from about 1 to 10 carbon atoms (e.g., alkyl ethers, alkyl sulfides, etc.); each $R_1$ is, independently, H or a $C_1$-$C_4$ alkyl (e.g., methyl, ethyl, etc.); each g is, independently, an integer value ranging from about 1 to 35; and h is an integer value ranging from about 1 to 22.

Other suitable acrylate functionalized compounds include bisphenol A derivatives having the general formula (V):

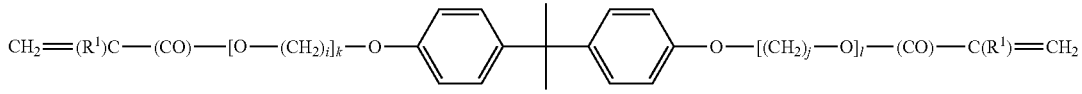

(V)

where each $R^1$ is, independently, H or a $C_1$-$C_4$ alkyl (e.g., methyl, ethyl, etc.); i and j are each, independently, integer values ranging from about 1 to 10; and k and l are each, independently, integer values of at least 1 whose combined sum (i.e., k+l) ranges from about 2 to 135. In some embodiments, the combined sum of i and j (i.e., i+j) ranges from about 2 to 10. In some embodiments, i and j are each 2.

Yet other suitable acrylate functionalized compounds include bisphenol F derivatives having the general formula (VI):

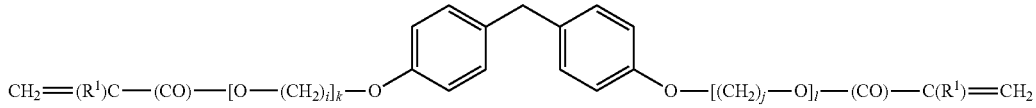

(VI)

where each $R^1$ is, independently, H or a $C_1$-$C_4$ alkyl (e.g., methyl, ethyl, etc.); i and j are each, independently, integer values ranging from about 1 to 10; and k and l are each, independently, integer values of at least 1 whose combined sum (i.e., k+l) ranges from about 2 to 135. In some embodiments, the combined sum of i and j (i.e., i+j) ranges from about 2 to 10. In some embodiments, i and j are each 2.

Commercially available acrylate functionalized reactive liquid modifiers include SR602 (an ethoxylated (10) bisphenol A diacrylate available from Sartomer Company, Inc. in Exton, Pa., USA).

Acrylamide Functionalized Compounds

Acrylamide functionalized compounds may be mono-, di- or poly-functionalized compounds. Suitable acrylamide functionalized compounds may be derived from the reaction of an oligomer of caprolactone with an azlactone as shown below (Scheme I).

Y represents a branched or linear alkyl chain having from about 1 to 10 carbon atoms (e.g., methyl, ethyl, propyl, isopropyl, n-butyl, t-butyl, etc.) or a heteroalkyl chain having from about 1 to 10 carbon atoms (e.g., alkyl ethers, alkyl sulfides, etc.). Each m is, independently, an integer value ranging from about 1 to 20. n is an integer value ranging from about 1 to 5.

$R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having about 4 to 12 carbon atoms. Each p is, independently, 0 or 1.

In some embodiments, the azlactone is 2-vinyl-4,4-dimethylazlactone.

In some embodiments, the acrylamide functionalized compound is a bisacrylamide (VII) where Y is an alkyl ether (—$CH_2CH_2OCH_2CH_2$—), m is 5, n is 2, p is 0 and $R^2$ and $R^3$ are each a methyl group (synthesis provided in Examples section).

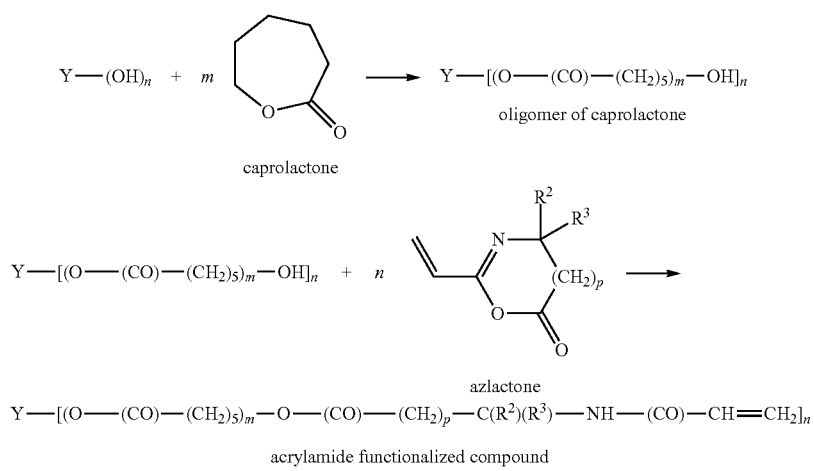

(VII)

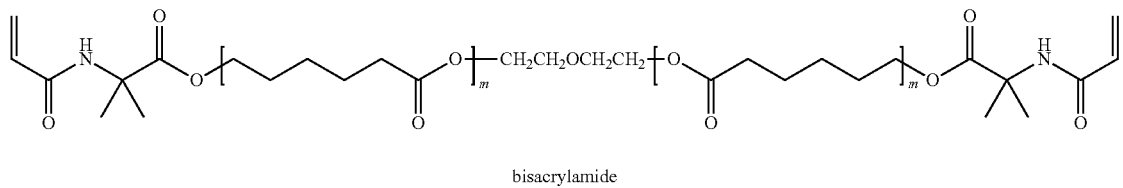

bisacrylamide

Other suitable acrylamide functionalized compounds may be derived from the reaction of an alkoxylated bisphenol A with an azlactone as shown below (Scheme II).

Scheme II

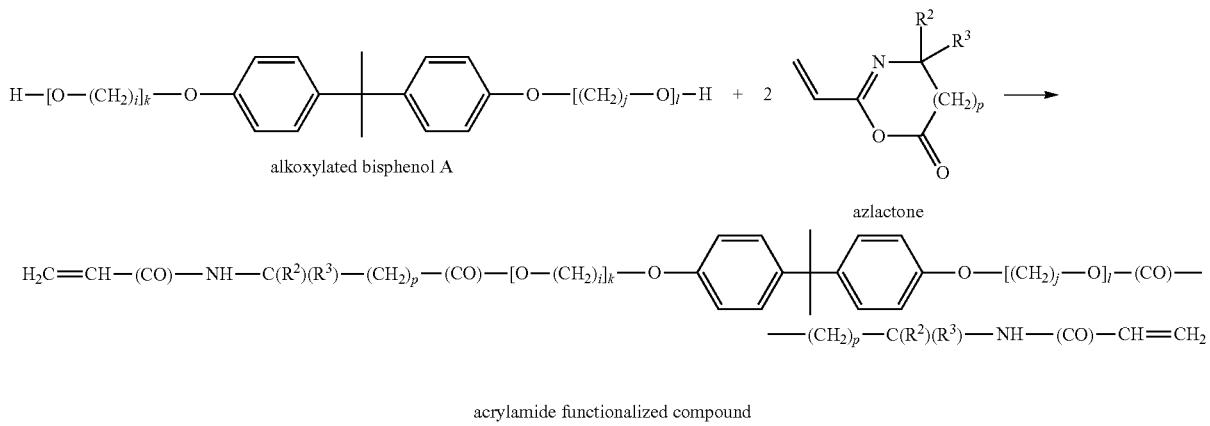

i and j are each, independently, integer values ranging from about 1 to 10. In some embodiments, the combined sum of i and j (i.e., i+j) ranges from about 2 to 10. In some embodiments, i and j are each 2.

k and l are each, independently, integer values of at least 1 whose combined sum (i.e., k+l) ranges from about 2 to 120.

$R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having about 4 to 12 carbon atoms. Each p is, independently, 0 or 1.

In some embodiments, the azlactone is 2-vinyl-4,4-dimethylazlactone.

Yet other suitable acrylamide functionalized compounds may be derived from the reaction of an alkoxylated bisphenol F with an azlactone as shown below (Scheme III).

Scheme III

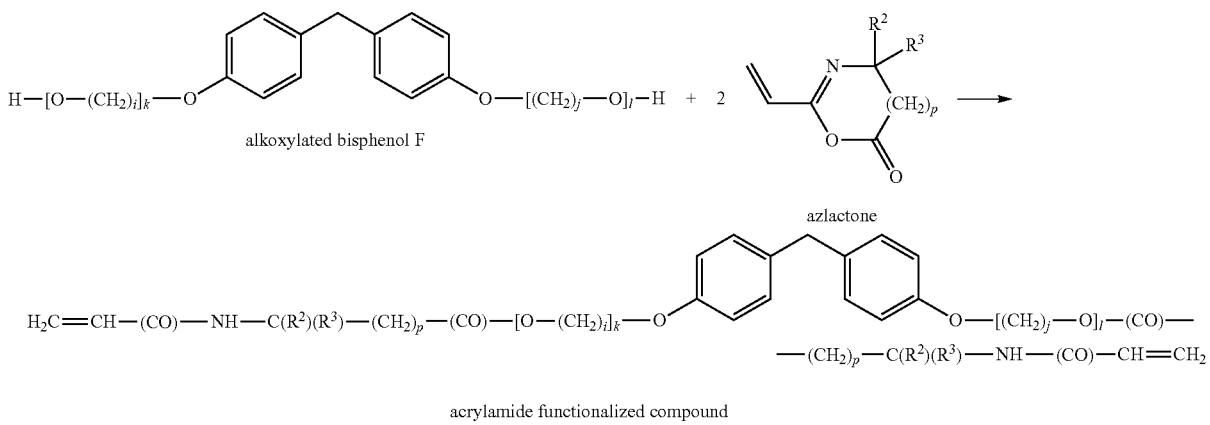

i and j are each, independently, integer values ranging from about 1 to 10. In some embodiments, the combined sum of i and j (i.e., i+j) ranges from about 2 to 10. In some embodiments, i and j are each 2.

k and l are each, independently, integer values of at least 1 whose combined sum (i.e., k+l) ranges from about 2 to 120.

$R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having about 4 to 12 carbon atoms. Each p is, independently, 0 or 1.

In some embodiments, the azlactone is 2-vinyl-4,4-dimethylazlactone.

Oxalic Amide Functionalized Compounds

Oxalic amide compounds may be functionalized di- or poly-functionalized compounds. Suitable oxalic amide functionalized compounds may be derived from the reaction of a diamine with a dialkyl oxalate as shown below (Scheme IV).

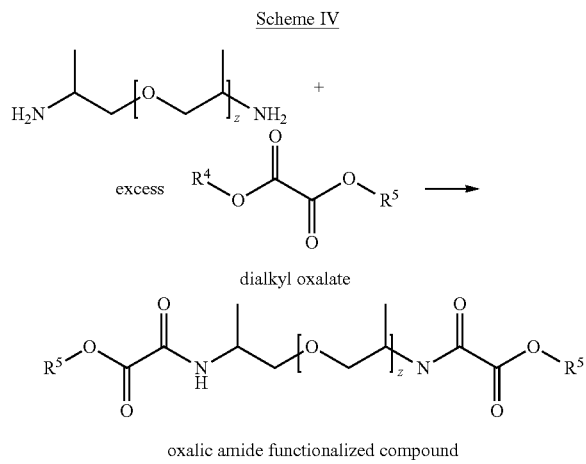

z is an integer value ranging from about 1 to 75. In some embodiments, z is 6.

$R^4$ and $R^5$ are each, independently, an alkyl group having from about 1 to 4 carbon atoms, a cycloalkyl group having from about 3 to 12 carbon atoms, or an aromatic group having from about 6 to 12 carbon atoms. In some embodiments, $R^4$ and $R^5$ are each an ethyl group.

In some embodiments, the oxalic amide functionalized compound is DEO-400 (synthesis provided in Examples section) where z is 5-6 and $R^4$ and $R^5$ are each ethyl groups.

Another suitable oxalic amide functionalized compound may be derived from the reaction of a polyamine with a dialkyl oxalate as shown below (Scheme V).

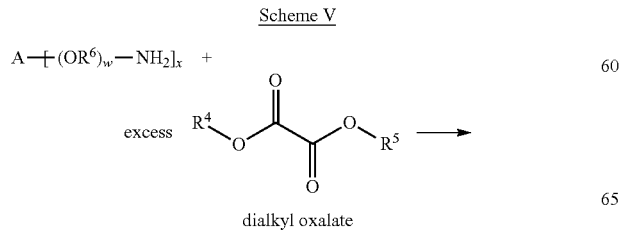

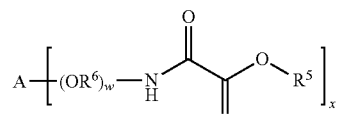

oxalic amide functionalized compound

A represents a branched or linear alkyl chain having from about 1 to 10 carbon atoms (e.g., methyl, ethyl, propyl, isopropyl, n-butyl, t-butyl, etc.). $R^6$ is a branched or linear alkyl chain having from about 1 to 5 carbon atoms. Each w is, independently, an integer value ranging from about 1 to 130. x is an integer value ranging from about 1 to 40.

$R^4$ and $R^5$ are each, independently, an alkyl group having from about 1 to 4 carbon atoms, a cycloalkyl group having from about 3 to 12 carbon atoms, or an aromatic group having from about 6 to 12 carbon atoms. In some embodiments, $R^4$ and $R^5$ are each an ethyl group.

Acetoacetoxy Functionalized Urethanes

Acetoacetoxy functionalized urethanes may be mono-, di- or poly-functionalized compounds prepared by capping one or more hydroxyl groups of oligourethane polyols with acetoacetoxy functional groups. Preferably acetoacetoxy functionalized urethanes are isocyanate free. In some embodiments, the acetoacetoxy functionalized urethanes are di-functionalized.

Exemplary acetoacetoxy functionalized urethanes include AcAcUD and AcAcXM (synthesis provided in the Examples section below).

Acetoacetoxy Functionalized Polyalkenes

Acetoacetoxy functionalized polyalkenes may be mono-, di- or poly-functionalized compounds. Suitable acetoacetoxy functionalized polyalkenes include those having general formula (VIII).

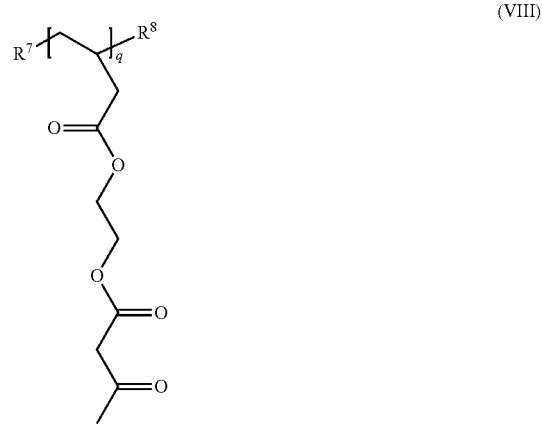

q represents the average number of acetoacetoxy groups per molecule and is an integer and a non-integer number ranging from about 1 to about 10. For example, in some embodiments, n ranges from about 2 to about 5. This includes embodiments where n is about 4.6. In other embodiments, n ranges from about 7 to about 10. This includes embodiments where n is about 9.

$R^7$ is H or an initiator fragment from a thermally decomposing initiator. Thermally decomposing initiators generally fall into two classes of compounds: azo- and peroxy-type compounds. Azo-type compounds are a widely used class of thermally decomposing initiators that generate both carbon- and oxygen-centered radicals by either C—N (dialkyl diazenes) or O—N (dialkyl hyponitrites) bond scission driven by the expulsion of a stable nitrogen molecule. Most of the azo-type compounds generate two identical radical species upon fragmentation. Exemplary azo-type compounds are provided below.

| Azo-Type Compounds | Initiator Fragments |
|---|---|
| 2,2'-azobisisobutyronitrile | |
| dimethyl 2,2'-azobisisobutyrate | |
| 1,1'-azobis(1-cyclohexanecarbonitrile) | |
| 2,2'-azobis-2,4-dimethylvaleronitrile | |
| 2,2'-azobis-(2-methylpropionamidine)dihydrochloride | |
| 4,4-azobis(4-cyanovaleric acid) | |

Peroxy-type compounds are thermally decomposing initiators that generate oxygen-centered radicals by O—O bond scission. Exemplary peroxy-type compounds are provided below.

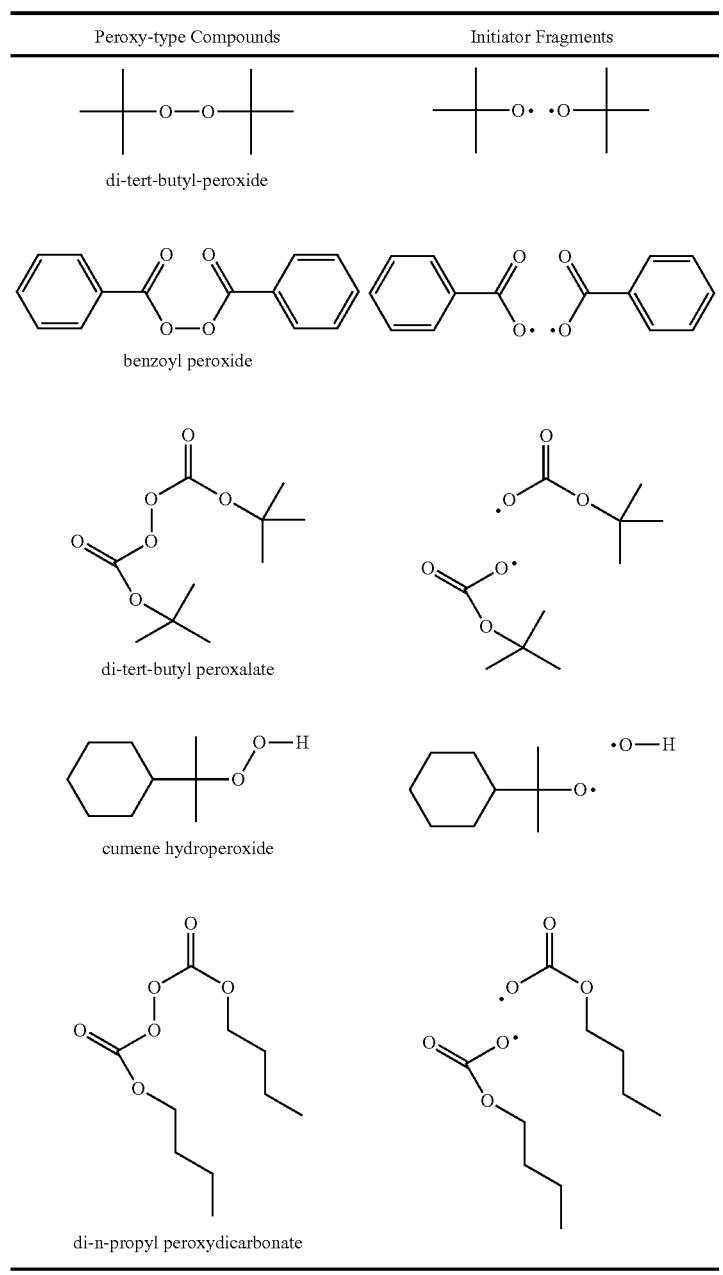

Other suitable peroxy-type compounds include 1,1-bis(tert-amylperoxy)cyclohexane, 1,1-bis(tert-butylperoxy)-3,3,5-trimethylcyclohexane, 1,1-bis(tert-butylperoxy)cyclohexane, 2,2-bis(tert-butylperoxy)butane, 2,4-pentandione peroxide, 2,5-bis(tert-butylperoxy)-2,5-dimethylhexane, 2-butanone peroxide, di-tert-amyl peroxide, dicumyl peroxide, lauroyl peroxide, tert-butyl hydroperoxide, tert-butyl peracetate, tert-butyl peroxide, tert-butyl peroxybenzoate, and tert-butylperoxy 2-ethylhexyl carbonate.

$R^8$ is H, an initiator fragment from a thermally decomposing initiator, or a thioester represented by formula (IX):

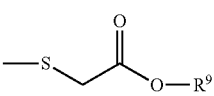

(IX)

where $R^9$ is a $C_1$-$C_{12}$ linear alkyl, a $C_1$-$C_{12}$ branched alkyl or a $C_1$-$C_{12}$ cyclic alkyl (e.g., methyl, ethyl, propyl, butyl, sec-butyl, tert-butyl, isooctyl, etc.). This includes embodiments where $R^9$ is isooctyl.

In some embodiments, the reactive liquid modifier of the present invention is MaAcAc 1000 MW Oligomer (synthesis provided in Examples section) where q is about 4.6, $R^7$ is a tert-butyl group, $R^8$ is general formula (IX) and $R^9$ is isooctyl.

In some embodiments, the reactive liquid modifier of the present invention is MaAcAc 2000 MW Oligomer (synthesis provided in Examples section) where q is about 9, $R^7$ is a tert-butyl group, $R^8$ is general formula (IX) and $R^9$ is isooctyl.

In some embodiments of the present invention, the structural adhesives comprise at least about 5% by weight reactive liquid modifier, in some embodiments at least about 8% by weight reactive liquid modifier, and in some embodiments at least about 10% by weight reactive liquid modifier. In some embodiments of the present invention, the structural adhesives comprise less than about 20% by weight reactive liquid modifier, in some embodiments less than about 15% by weight reactive liquid modifier, and in some embodiments less than about 12% by weight reactive liquid modifier.

In some embodiments of the present invention, the structural adhesives comprise from about 5% to about 20% by weight reactive liquid modifier. In other embodiments, the structural adhesives comprise from about 6% to about 12% by weight reactive liquid modifier. In yet other embodiments, the structural adhesives comprise from about 6% to about 10% by weight reactive liquid modifier.

Epoxy Resin Compositions

The reactive liquid modifiers of the present invention may be incorporated into epoxy resin compositions comprising a curable epoxy resin and an amine curing agent. The epoxy resin compositions may also include toughening agents, secondary curatives, radical initiators, reactive diluents, and combinations thereof, as well as other ingredients known to those skilled in the art (e.g., fillers, colorants, viscosity modifiers, fire retardant agents, mold release agents, adhesion promoters, etc.). The epoxy resin compositions of the present invention may be used in any of the various industries currently employing epoxy resins. This includes applications in adhesives, composites, coatings and laminates.

Curable Epoxy Resins

Epoxy resin compositions of the present invention comprise at least one curable epoxy resin. The epoxy resins may be monomeric, dimeric, oligomeric or polymeric epoxy materials containing at least one epoxy functional group per molecule. Such resins may be aromatic or aliphatic, cyclic or acyclic, monofunctional or polyfunctional. The backbone of the resin may be of any type, and substituent groups thereon can be any group not having a nucleophilic group or electrophilic group (such as an active hydrogen atom) which is reactive with an oxirane ring. Exemplary substituent groups include halogens, ester groups, ethers, sulfonate groups, siloxane groups, nitro groups, amide groups, nitrile groups, and phosphate groups.

The molecular weights of the epoxy resins may range from about 100 g/mole for monomeric or oligomeric resins to 50,000 g/mole or more for polymeric resins. Suitable epoxy resins are typically a liquid at room temperature. However, soluble solid epoxy resins may also be used. Epoxy resins may be used alone or in combination. In some embodiments, the epoxy component comprises a mixture of two or more epoxy resins in order to modify and adapt the mechanical properties of the cross-linked epoxy resin composition with respect to specific requirements.

Types of epoxy resins that can be used include, for example, the reaction product of bisphenol A and epichlorohydrin, the reaction product of phenol and formaldehyde (novolac resin) and epichlorohydrin, peracid epoxies, glycidyl esters, glycidyl ethers, the reaction product of epichlorohydrin and p-amino phenol, the reaction product of epichlorohydrin and glyoxal tetraphenol and the like.

Epoxides that are particularly useful in the present invention are of the glycidyl ether type. Suitable glycidyl ether epoxides may include those in general formula (VII):

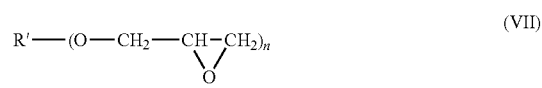

(VII)

wherein R' is an n valent organic residue that may include, for example, an alkyl group, an alkyl ether group, or an aryl group; and n is at least 1. In some embodiments R' is a poly(alkylene oxide). In some embodiments, n ranges from 1 to 4.

Suitable glycidyl ether epoxides of formula (VII) include glycidyl ethers of bisphenol A and F, aliphatic diols and cycloaliphatic diols. In some embodiments, the glycidyl ether epoxides of formula (VII) have a molecular weight in the range of from about 170 g/mol to about 10,000 g/mol. In other embodiments, the glycidyl ether epoxides of formula (I) have a molecular weight in the range of from about 200 g/mol to about 3,000 g/mol.

Useful glycidyl ether epoxides of formula (VII) include linear polymeric epoxides having terminal epoxy groups (e.g., a diglycidyl ether of polyoxyalkylene glycol) and aromatic glycidyl ethers (e.g., those prepared by reacting a dihydric phenol with an excess of epichlorohydrin). Examples of useful dihydric phenols include resorcinol, catechol, hydroquinone, and the polynuclear phenols including p,p'-dihydroxydibenzyl, p,p'-dihydroxyphenylsulfone, p,p'-dihydroxybenzophenone, 2,2'-dihydroxyphenyl sulfone, p,p'-dihydroxybenzophenone, 2,2-dihydroxy-1,1-dinaphrhylmethane, and the 2,2', 2,3', 2,4', 3,3', 3,4', and 4,4' isomers of dihydroxydiphenylmethane, dihydroxydiphenyldimethylmethane, dihydroxydiphenylethylmethylmethane, dihydroxydiphenylmethylpropylmethane, dihydroxydiphenylethylphenylmethane, dihydroxydiphenylpropylenphenylmethane, dihydroxydiphenylbutylphenylmethane, dihydroxydiphenyltolylethane, dihydroxydiphenyltolylmethylmethane, dihydroxydiphenyldicyclohexylmethane, and dihydroxydiphenylcyclohexane.

Suitable commercially available aromatic and aliphatic epoxides include diglycidylether of bisphenol A (e.g., EPON 828, EPON 872, EPON 1001, EPON 1310 and EPONEX 1510 available from Hexion Specialty Chemicals GmbH in Rosbach, Germany), DER-331, DER-332, and DER-334 (available from Dow Chemical Co. in Midland, Mich., USA); diglycidyl ether of bisphenol F (e.g., EPICLON 830 available from Dainippon Ink and Chemicals, Inc.); $PEG_{1000}DGE$ (available from Polysciences, Inc. in Warrington, Pa., USA); silicone resins containing diglycidyl epoxy functionality; flame retardant epoxy resins (e.g., DER 580, a brominated bisphenol type epoxy resin available from Dow Chemical Co. in Midland, Mich., USA); 1,4-dimethanol cyclohexyl diglycidyl ether; and 1,4-butanediol diglycidyl ether. Other epoxy resins based on bisphenols are commercially available under the tradenames D.E.N., EPALLOY and EPILOX.

In some embodiments of the present invention, the epoxy resin compositions comprise at least about 20% by weight curable epoxy resin, in some embodiments at least about 40% by weight curable epoxy resin, and in some embodiments at least about 50% by weight curable epoxy resin. In some embodiments of the present invention, the epoxy resin compositions comprise less than about 90% by weight curable epoxy resin, in some embodiments less than about 80% by weight curable epoxy resin, and in some embodiments less than about 70% by weight curable epoxy resin.

In some embodiments of the present invention, the epoxy resin compositions comprise from about 20% to about 90% by weight curable epoxy resin. In other embodiments, the epoxy resin compositions comprise from about 40% to about 70% by weight curable epoxy resin. In yet other embodiments, the epoxy resin compositions comprise from about 50% to about 70% by weight curable epoxy resin.

Amine Curing Agents

Epoxy resin compositions of the present invention also comprise at least one curing agent capable of cross-linking the curable epoxy resin. The amine curing agent may also be used to cross-link some types of reactive liquid modifiers. Typically these agents are primary or secondary amines. The amines may be aliphatic, cycloaliphatic, aromatic, or aromatic structures having one or more amino moieties.

Suitable amine curing agents include those amines having the general formula (VIII):

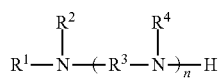

(VIII)

wherein $R^1$, $R^2$, $R^3$ and $R^4$ are each independently hydrogen or a hydrocarbon containing from about 1 to 15 carbon atoms, wherein the hydrocarbons include polyethers; and the value for n ranges from about 1 to 10. In some embodiments, the curing agent is a primary amine. In the same, or other, embodiments, $R^3$ is a polyetheralkyl.

Exemplary amine curing agents include ethylene diamine, diethylene diamine, diethylene triamine, triethylene tetramine, propylene diamine, tetraethylene pentamine, hexaethylene heptamine, hexamethylene diamine, 2-methyl-1,5-pentamethylene-diamine, 4,7,10-trioxatridecan-1,13-diamine, aminoethylpiperazine and the like.

In some embodiments, the amine curing agent is a polyether amine having one or more amine moieties, including those polyether amines that can be derived from polypropylene oxide or polyethylene oxide. Commercially available polyether amines include the JEFFAMINE™ series of polyether polyamines (available from Huntsman Corporation in The Woodlands, Tex., USA) and 4,7,10-trioxatridecane-1,13-diamine (TTD) (available from TCI America in Portland, Oreg., USA).

The primary or secondary amine hydrogens on the amine curing agent will react stoichiometrically with the epoxy moieties on the curable epoxy resin to form a cross-linked epoxy network. The molar ratio of epoxy moieties to primary or secondary amine hydrogens can be adjusted to achieve desired performance. In some embodiments, the epoxy resin compositions of the present invention have a molar ratio of epoxy moieties on the curable epoxy resin to amine hydrogens on the amine curing agent ranging from about 0.5:1 to about 3:1. This includes embodiments where the molar ratio is about 2:1 or about 1:1. If other ingredients within the epoxy resin composition also react with the amine curing agent (e.g., some types of reactive liquid modifiers), the amount of amine curing agent in the epoxy resin composition may be increased accordingly.

In some embodiments of the present invention, the epoxy resin compositions comprise at least about 3% by weight amine curing agent, in some embodiments at least about 5% by weight amine curing agent, and in some embodiments at least about 10% by weight amine curing agent. In some embodiments of the present invention, the epoxy resin compositions comprise less than about 30% by weight amine curing agent, in some embodiments less than about 20% by weight amine curing agent, and in some embodiments less than about 15% by weight amine curing agent.

In some embodiments of the present invention, the epoxy resin compositions comprise from about 3% to about 30% by weight amine curing agent. In other embodiments, the epoxy resin compositions comprise from about 5% to about 15% by weight amine curing agent.

Secondary Curatives

Structural adhesives of the present invention may optionally comprise a secondary curative. Secondary curatives according to the invention include imidazoles, imidazole-salts, imidazolines or aromatic tertiary amines including those having the structure of formula (IX):

(IX)

wherein
$R^1$ is H or alkyl (e.g., methyl or ethyl);
$R^2$ is $CHNR^5R^6$;
$R^3$ and $R^4$ may be, independently from each other, present or absent and when present $R^3$ and $R^4$ are $CHNR^5R^6$; and
$R^5$ and $R^6$ are, independent from each other, alkyl (e.g., $CH_3$ or $CH_2CH_3$).

An exemplary secondary curative is tris-2,4,6-(dimethylaminomethyl)phenol (available as ANCAMINE K54 from Air Products Chemicals in Europe B.V).

Other secondary curatives may include diisocyanates (e.g., toluene diisocyanate, hexamethylene diisocyanate, diphenylmethane diisocyanate, isophorone diisocyanate, and trimethylhexamethylene diisocyanate).

Toughening Agents

Toughening agents are polymers, other than the curable epoxy resins or the reactive liquid modifiers (described above), capable of increasing the toughness of cured epoxy resins. The toughness can be measured by the peel strength of the cured compositions. Typical toughening agents include core/shell polymers, butadiene-nitrile rubbers, acrylic polymers and copolymers, etc. Commercially available toughening agents include a polyether diamine (available as Dynamar™ Polyetherdiamine HC 1101 from 3M Corporation in St. Paul, Minn., USA) and carboxyl-terminated butadiene acrylonitrile (available from Emerald Chemical in Alfred, Me., USA).

In some embodiments, the epoxy resin compositions of the present invention comprise from about 5% to about 55% by weight toughening agent. In other embodiments, the epoxy resin compositions comprise from about 5% to about 30% by weight toughening agent. In yet other embodiments, the epoxy resin compositions comprise from about 5% to about 15% by weight toughening agent.

Suitable toughening agents include core/shell polymers. A core/shell polymer is understood to mean a graft polymer having a core comprising a graftable elastomer, which means an elastomer on which the shell can be grafted. The elastomer may have a glass transition temperature lower than 0° C. Typically the core comprises or consists of a polymer selected from the group consisting of a butadiene polymer or copolymer, an acrylonitrile polymer or copolymer, an acrylate polymer or copolymer and combinations thereof. The polymers or copolymers may be cross-linked or not cross-linked. In some embodiments, the core polymers are cross-linked.

Onto the core is grafted one or more polymers, the "shell". The shell polymer typically has a high glass transition temperature, i.e. a glass transition temperature greater than 26° C. The glass transition temperature may be determined by dynamic mechanical thermo analysis (DMTA) ("Polymer Chemistry, The Basic Concepts, Paul C. Hiemenz, Marcel Dekker 1984).

The "shell" polymer may be selected from the group consisting of a styrene polymer or copolymer, a methacrylate polymer or copolymer, an acrylonitrile polymer or copolymer, or combinations thereof. The thus created "shell" may be further functionalized with epoxy groups or acid groups. Functionalization of the "shell" may be achieved, for example, by copolymerization with glycidylmethacrylate or acrylic acid. In particular, the shell may comprise acetoacetoxy moieties in which case the amount of acetoacetoxy-functionalized polymer may be reduced, or it may be completely replaced by the acetoacetoxy-functionalized core/shell polymer.

The shell of suitable core/shell polymers may comprise a polyacrylate polymer or copolymer shell such as, for example, a polymethylmethacrylate shell. The polyacrylate shell, such as the polymethylmethacrylate shell, may not be cross-linked.

The core of suitable core/shell polymers may comprise a butadiene polymer or copolymer, a styrene polymer or copolymer, or a butadiene-styrene copolymer. The polymers or copolymers making up the core, such as a butadiene-styrene core, may be cross-linked.

In some embodiments, the core/shell polymer according to the present invention may have a particle size from about 10 nm to about 1,000 nm. In other embodiments, the core/shell polymer may have a particle size from about 150 nm to about 500 nm.

Suitable core/shell polymers and their preparation are for example described in U.S. Pat. No. 4,778,851. Commercially available core/shell polymers may include, for example, PARALOID EXL 2600 and 2691 (available from Rohm & Haas Company in Philadelphia, Pa., USA) and KANE ACE MX120 (available from Kaneka in Belgium).

Radical Initiators

Compositions of the present invention that comprise an acrylate functionalized reactive liquid modifier or an acrylamide functionalized reactive liquid modifier also include one or more radical initiators that polymerize the ethylenically unsaturated acrylate or acrylamide moieties. Radical initiators may include thermal initiators, such as peroxides and azo compounds. Exemplary peroxide thermal initiators may include acyl peroxides (e.g., acetyl peroxide and benzoyl peroxide), alkyl peroxides (e.g., cumyl peroxides and t-butyl peroxides), hydroperoxides (e.g., cumyl hydroperoxides and t-butyl hydroperoxides) and peresters (e.g., t-butyl perbenzoate). Exemplary azo thermal initiators may include 2,2'-azobisisobutyronitrile and VAZO-52 and VAZO-67 (available from DuPont Chemicals in Wilmington, Del., USA).

Radical initiators may also include redox initiators comprising at least one oxidant and at least one reductant. Various redox systems may optionally including microencapsulated reducing and/or oxidizing agents. The oxidizing agent reacts with, or otherwise cooperates with, the reducing agent to produce free radicals. The free radicals are capable of initiating polymerization of the ethylenically unsaturated acrylate or acrylamide moieties.

Suitable oxidizing agents may include: persulfates (e.g., sodium, potassium, ammonium, and alkyl ammonium persulfates); peroxides or peroxide salts (e.g., hydrogen peroxide, benzoyl peroxide, and hydroperoxides including, for example cumene hydroperoxide, tert-butyl hydroperoxide, tert-amyl hydroperoxide, and 2,5-dihydroperoxy-2,5-dimethylhexane); salts of cobalt(III) and iron(III); perboric acid and its salts; salts of a permanganate anion, and combinations thereof.

Suitable reducing agents may include: amines (e.g., aromatic amines); ascorbic acid; metal complexed ascorbic acid; cobalt(II) chloride; ferrous chloride; ferrous sulfate; hydrazine; hydroxylamine; oxalic acid; thiourea; and salts of dithionite, thiosulfate, benzene sulfinate, or sulfite anions.

Exemplary redox initiators may include the benzoyl peroxide/N,N-dialkylaniline initiator system and the benzoyl peroxide/N,N-bis(2-hydroxyethyl)-p-toluidine initiator system.

In some embodiments, the radical initiator comprises at least one of VAZO-52, VAZO-67, and combinations thereof. In other embodiments, the radical initiator comprises the benzoyl peroxide/N,N-bis(2-hydroxyethyl)-p-toluidine redox initiator system.

The amount of free radical initiator can be sufficient to cause polymerization of the epoxy resin composition and form an IPN. In some embodiments, the epoxy resin compositions of the present invention comprise from about 0.01% to about 5% by weight initiator. This includes embodiments where the epoxy resin compositions comprise from about 0.1% to about 2% by weight initiator.

Reactive Diluents

Reactive diluents may optionally be added to control the flow characteristics of the epoxy resin composition. Suitable diluents can have at least one reactive terminal end portion and, preferably, a saturated or unsaturated cyclic backbone. Reactive terminal end portions include glycidyl ether. Examples of suitable diluents include the diglycidyl ether of resorcinol, diglycidyl ether of cyclohexane dimethanol, diglycidyl ether of neopentyl glycol and triglycidyl ether of trimethylolpropane. Commercially available reactive diluents are for example Reactive Diluent 107 (available from Hexion Specialty Chemical in Houston, Tex.) and EPODIL 757 (available from Air Products and Chemical Inc. in Allentown, Pa.).

In some embodiments, the epoxy resin composition may contain from about 0.001% to 25% by weight reactive diluent.

Curing Epoxy Resin Compositions

To produce IPNs in the epoxy resin compositions of the present invention, the cure rate of the reactive liquid modifier is preferably greater than that of the epoxy resin. If the epoxy resin cures before the reactive liquid modifier, "domaining" may occur, causing unacceptable discontinuities in the epoxy resin composition. Thus, the chemical and physical properties of the final IPN are strongly affected by the relative rates of epoxy resin and reactive liquid modifier curing.

Generally, when the reactive liquid modifier is an oxalic amide functionalized compound, an acetoacetoxy functionalized urethane or an acetoacetoxy functionalized polyalkene, the amine curing agent will substantially polymerize the reactive liquid modifier prior to curing the epoxy resin. When the reactive liquid modifier is an acrylate functionalized compound or an acrylamide functionalized compound, radical initiators and/or polymerization temperatures are selected such that the reactive liquid modifiers polymerize before substantial curing of the epoxy resin.

From a chemical standpoint, IPNs are whole unit structures formed of two entirely different types of polymers that exhibit physical properties of both polymers. If the reactive liquid modifier is compatible with the epoxy resin, the glass transition temperature of the epoxy-rich phase will lie somewhere in-between the Tg of the epoxy resin and the Tg of the polymerized liquid modifier, where the amount of change is determined by the amount of reactive liquid modifier in the composition. If, on the other hand, the reactive liquid modifier is incompatible with the epoxy resin, phase separation will occur, and the glass transition temperature of the epoxy-rich phase will remain largely unchanged by the amount of reactive liquid modifier present. Therefore, compositions of the present invention will typically exhibit glass transition temperatures either lower or higher than corresponding compositions without the reactive liquid modifier.

The epoxy resin compositions of the present invention are typically cured in a two step process. In the first step (first cure), the primary reaction is the polymerization of the reactive liquid modifier. In the second step (second cure), the primary reaction is the cross-linking of the epoxy resin.

The conditions of the primary cure will depend to some extent upon the nature of the reactive liquid modifiers. In some embodiments, the primary cure is carried out at room temperature for at least 3 hours. This includes embodiments where the primary cure is carried out at room temperature for at least 24 hours. This also includes embodiments where the primary cure is carried out at room temperature for at least 72 hours.

In some embodiments, the secondary cure is carried out at elevated temperatures ranging from about 80° C. to about 200° C. The length of time over which the adhesive is cured will vary with the desired properties.

In applications where the epoxy resin composition is used as an adhesive, the epoxy resin composition may reach a desirable cohesive strength after short heat curing periods. Since the cohesive strength can still increase when curing the composition at the same conditions for longer periods, this kind of curing is referred to herein as partial curing. In principle, partial curing can be carried out by any kind of heating. In some embodiments, induction curing (e.g., spot induction curing or ring induction curing) may be used for partial curing. Induction curing is a non-contact method of heating using electric power to generate heat in conducting materials by placing an inductor coil through which an alternating current is passed in proximity to the material. The alternating current in the work coil sets up an electromagnetic field that creates a circulating current in the work piece. This circulating current in the work piece flows against the resistivity of the material and generates heat. Induction curing equipment can be commercially obtained, for example, EWS from IFF-GmbH in Ismaning, Germany.

In yet a further embodiment, the epoxy resin compositions may undergo an induction cure, followed by a room temperature cure and a higher temperature post cure.

Applications

The reactive liquid modifiers of the present invention and the epoxy resin compositions to which they are added may be used in any application where epoxy resins are employed. Applications for epoxy resins include paints and coatings, adhesives, industrial tooling and composites, electrical systems and electronics, and aerospace applications.

The epoxy resin compositions of the present invention may be used as primer coatings to improve the adhesion of automotive and marine paints, especially on metal surfaces where corrosion (rusting) resistance is important. The epoxy resin compositions may also be used to coat metal cans and containers to prevent rusting. This has particular application in the food industry where epoxy resin compositions may be used to coat cans containing acidic foods such as tomatoes. The epoxy resin compositions may also be used for high performance and decorative flooring applications, including terrazzo flooring, chip flooring and colored aggregate flooring.

The epoxy resins may also be used in a class of adhesives called "structural adhesives" or "engineering adhesives." These high-performance adhesives are used in the construction of aircraft, automobiles, bicycles, boats, golf clubs, skis, snow boards, and other applications where high strength bonds are required. The epoxy resin compositions can be used to suit almost any application. They make particularly good adhesives for wood, metal, glass, stone, and some plastics.

The epoxy resin compositions may also be used in industrial tooling applications to produce molds, master models, laminates, castings, fixtures, and other industrial production aids. This so-called "plastic tooling" replaces metal, wood and other traditional materials, and generally improves efficiency and either lowers the overall cost or shortens the lead-time for many industrial processes. The epoxy resin compositions may also be used in producing fiber-reinforced or composite parts.

The epoxy resin compositions may be used in the electronics industry, and may be employed in motors, generators, transformers, switchgear, bushings, and insulators. The epoxy resin compositions may also be used as the primary resin in overmolding integrated circuits, transistors and hybrid circuits, and in making printed circuit boards.

In the aerospace industry, the epoxy resin compositions may be used as a structural matrix material which is then reinforced by fiber. Typical fiber reinforcements include glass, carbon, Kevlar, and boron. The epoxy resin compositions may also be used as structural glue and boid filler.

The above uses are merely representative of the various ways in which the reactive liquid modifiers, and the epoxy resin compositions to which they are added, may be used. The list is by no means exhaustive.

One application for the reactive liquid modifiers of the present invention is in two-part epoxy-based structural adhesives.

Two-Part Epoxy-Based Structural Adhesives

Reactive liquid modifiers of the present invention may be used in two-part epoxy-base structural adhesives. The two-part epoxy-based structural adhesives comprise a Part A and, separate therefrom, a Part B. Part A comprises an amine curing agent and Part B comprises a curable epoxy resin. Part A may also comprise curable epoxy resin in addition to that in Part B. As for any remaining ingredients (e.g., toughening agents, reactive liquid modifiers, secondary curatives, radical initiators, reactive diluents, etc.), compounds with epoxy reactive groups are added to Part A, compounds with amine reactive groups are added to Part B, and compounds that do not react with either an epoxy reactive group or an amine reactive group may be added to Part A, Part B or a combination thereof. Alternatively, a separate part for one or more of these ingredients may be contemplated.

The amounts of Part A and Part B combined to make the adhesive will depend upon the desired epoxy to amine curing agent in the cross-linked epoxy network. In some embodiments, the structural adhesives of the present invention have a molar ratio of epoxy moieties on the curable epoxy resin to amine hydrogens on the amine curing agent ranging from about 0.5:1 to about 3:1. This includes embodiments where the molar ratio is about 2:1 or about 1:1. If other ingredients within the structural adhesive also react with the amine curing agent, the amount of amine curing agent in the structural adhesive may be increased accordingly. The respective amounts of Part A and Part B are preferably mixed together immediately prior to use.

In some embodiments, the structural adhesive comprise a curable epoxy resin, an amine curing agent, a toughening agent and a reactive liquid modifier. In other embodiments, the structural adhesives comprise a curable epoxy resin, an amine curing agent, a secondary curative, a toughening agent, and a reactive liquid modifier. In yet other embodiments, the structural adhesives comprise a curable epoxy resin, an amine curing agent, a secondary curative, a toughening agent, a reactive liquid modifier, and a reactive diluent.

Curing

In order to generate the IPNs within the structural adhesive, the cure rate of the reactive liquid modifier is preferably greater than that of the epoxy resin. Generally, when the reactive liquid modifier is an oxalic amide functionalized compound, an acetoacetoxy functionalized urethane or an acetoacetoxy functionalized polyalkene, the amine curing agent will substantially polymerize the reactive liquid modifier prior to curing the epoxy resin (see Examples 2-4). When the reactive liquid modifier is an acrylate functionalized compound or an acrylamide functionalized compound, radical initiators and/or polymerization temperatures should be selected such that the reactive liquid modifiers polymerize before substantial curing of the epoxy resin (see Example 1).

Example 1 illustrates how polymerization rate of the reactive liquid modifier can effect the formation of an IPN and ultimately the quality of the structural adhesive. The acrylate functionalized reactive liquid modifier in ACRYLATE1 was polymerized as separate samples at 60° C. (ACRYLATE1-60) and 100° C. (ACRYLATE1-100) prior to curing of the epoxy resin. Polymerization rate of the reactive liquid modifier increases with temperature. Therefore, polymerization of the reactive liquid modifier will proceed further in the sample cured at 100° C. than in the sample cured at 60° C. during the same time period. As illustrated in FIG. 1, the glass transition temperature of ACRYLATE1-60 is similar to EPOXYST (a 1:1 epoxy adhesive without reactive liquid modifier). At 60° C., the reactive liquid modifier was unable to substantially polymerize prior to curing of the epoxy resin, resulting in phase separation between the reactive liquid modifier and the epoxy resin. Hence, the glass transition temperature is similar to that of cured epoxy resin. In contrast, ACRYLATE1-100 has a glass transition temperature significantly lower than EPOXYST. At 100° C., the reactive liquid modifier substantially polymerizes prior to curing of the epoxy resin, resulting in an IPN with properties of both the cured epoxy resin and polymerized reactive liquid modifier. Therefore, in some embodiments of the present invention, the reactive liquid modifier is polymerized prior to curing of the epoxy resin.

The conditions of the primary cure will depend to some extent upon the nature of the reactive liquid modifiers. In some embodiments, the primary cure is carried out at room temperature for at least 3 hours. This includes embodiments where the primary cure is carried out at room temperature for at least 24 hours. This also includes embodiments where the primary cure is carried out at room temperature for at least 72 hours. In other embodiments, the primary cure may be conducted at temperatures greater than room temperature. This includes embodiments where the primary cure is conducted at about 110° C. for about 30 minutes, or at about 110° C. for about 1 hour.

The secondary cure is typically carried out at elevated temperatures ranging from about 80° C. to about 200° C. The length of time over which the adhesive is cured will vary with the desired properties. In some embodiments, the secondary cure is carried out for 30 minutes at 180° C.

In some embodiments of the present invention, the structural adhesives are cured for 30 minutes at 110° C. followed by 30 minutes at 180° C.

Bond Strength

It is desirable for the two-part epoxy-based adhesive to build a strong, robust bond to one or more substrates upon curing. A bond is considered robust if the bond breaks apart cohesively at high shear values when tested in an overlap shear test and high T-peel values when tested in a T-peel test. The bonds may break in three different modes: (1) the adhesive splits apart, leaving portions of the adhesive adhered to both metal surfaces in a cohesive failure mode; (2) the adhesive pulls away from either metal surface in an adhesive failure mode; or (3) a combination of adhesive and cohesive failure. Structural adhesives of the present invention may exhibit a combination of adhesive and cohesive failure, more preferably cohesive failure during overlap shear testing and T-peel testing.

In some embodiments, structural adhesives of the present invention may have a lap shear strength of at least 1,000 psi when cured for 30 minutes at 110° C. followed by 30 minutes at 180° C. In other embodiments, the structural adhesives may have a lap shear strength of at least 2500 psi. In yet other embodiments, the structural adhesives may have a lap shear strength of at least 4000 psi.

In some embodiments, the structural adhesives of the present invention may have a T-peel strength of at least 30 lb/in-width when cured for 30 minutes at 110° C. followed by 30 minutes at 180° C. In other embodiments, the structural adhesives may have a T-peel strength of at least 50 lb/in-width. In yet other embodiments, the structural adhesives may have a T-peel strength of at least 60 lb/in-width.

Structural adhesives of the present invention may have a lap shear strength of at least 2500 psi and a T-peel strength of at least 30 lb/in-width when cured for 30 minutes at 110° C. followed by 30 minutes at 180° C. Additionally, structural adhesives of the present invention may have a lap shear strength of at least 2500 psi and a T-peel strength of at least 50 lb/in-width when cured for 30 minutes at 110° C. followed by 30 minutes at 180° C. Furthermore, structural adhesives of the present invention may have a lap shear strength of at least 4000 psi and a T-peel strength of at least 30 lb/in-width when cured at room temperature for about 18 hours followed by 180° for 30 minutes.

Application of Structural Adhesives

The present adhesive compositions may be used to supplement or completely eliminate a weld or mechanical fastener by applying the adhesive composition between two parts to be joined and curing the adhesive to form a bonded joint. Suitable substrates onto which the adhesive of the present invention may be applied include metals (e.g., steel, iron, copper, aluminum, etc., including alloys thereof), carbon fiber, glass fiber, glass, epoxy fiber composites, wood, and mixtures thereof. In some embodiments, at least one of the substrates is a metal. In other embodiments, both substrates are metal.

In areas of adhesive bonding, the adhesive can be applied as liquid, paste, and semi-solid or solid that can be liquefied upon heating, or the adhesive may be applied as a spray. It can be applied as a continuous bead, in intermediate dots, stripes, diagonals or any other geometrical form that will conform to forming a useful bond. In some embodiments, the adhesive composition is in a liquid or paste form.

The adhesive placement options may be augmented by welding or mechanical fastening. The welding can occur as spot welds, as continuous seam welds, or as any other welding technology that can cooperate with the adhesive composition to form a mechanically sound joint.

Structural adhesives may be used in vehicle assembly, such as the assembly of watercraft vehicles, aircraft vehicles or motorcraft vehicles (e.g., cars, motor bikes or bicycles). In particular, the structural adhesives may be used as hem-flange adhesives. The structural adhesives may also be used in body frame construction. The compositions may also be used as structural adhesives in architecture or as structural adhesives in household and industrial appliances.

The structural adhesives may be used as a metal-metal adhesive, metal-carbon fiber adhesive, carbon fiber-carbon fiber adhesive, metal-glass adhesive, and carbon fiber-glass adhesive.

Exemplary embodiments of the present invention are provided in the following examples. The following examples are presented to illustrate the present invention and methods for applying the present invention and to assist one of ordinary skill in making and using the same. The examples are not intended in any way to otherwise limit the scope of the invention.

EXAMPLES

Materials Employed

ANCAMINE K54 (available from Air Products in Allentown, Pa., USA) is a technical grade tris-2,4,6-dimethylaminomethyl-phenol catalytic tertiary amine additive.

BP (available from Aldrich Chemical Company in Milwaukee, Wis., USA) is benzoyl peroxide.

γ-Butyrolactone (available from Aldrich Chemical Company in Milwaukee, Wis., USA).

Polycaprolactone diol (available from Sigma-Aldrich Chemical Company in Milwaukee, Wis., USA—Catalog No. 18,941-3).

CPR-1250 Bisacrylamide (synthesis provided below) is an acrylamide reactive liquid modifier.

DBU (available from Aldrich Chemical Company in Milwaukee, Wis., USA) is 1,8-diazabicyclo[5.4.0]undec-7-ene.

DHEPT (available from TCI America in Portland, Oreg., USA) is N,N-Bis(2-hydroxyethyl)-p-toluidine

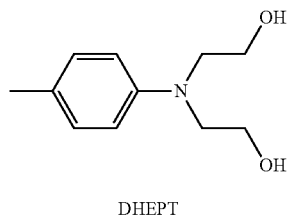

DHEPT

DEO-400 (synthesis provided below) is an oxamido ester terminated polypropylene oxide.

DER 331 (available from Dow Chemical Co. in Midland, Mich., USA) is the diglycidyl ether of bis-phenol A having an approximate epoxy equivalent weight of 187.5.

Diethyloxalate (available from Alfa Aesar in Ward Hill, Mass., USA).

EPODIL 757 (available from Air Products and Chemicals Inc. in Allentown, Pa., USA) is a reactive diluent based on 1,4-cyclohexandimethanoldiglycidylether.

EPON 828 (available from Hexion Specialty Chemicals in Houston, Tex., USA) is the diglycidyl ether of bis-phenol A having an approximate epoxy equivalent weight of 187.5.

Ethyl acetate (available from Alfa Aesar in Ward Hill, Mass., USA).

IOTGA (available from TCI America in Portland, Oreg., USA) is an isooctyl ester of thioglycidic acid.

JEFFAMINE® D-400 Polyetheramine (available from Hunstman Corporation in The Woodlands, Tex., USA).

K-FLEX XM-311 (available from King Industries in Norwalk, Conn., USA) is a polyurethane polyol.

K-FLEX UD-320-1000 (available from King Industries in Norwalk, Conn., USA) is a polyurethane polyol.

MaAcAc (available from Aldrich Chemical Company in Milwaukee, Wis., USA) is 2-(methacryloyloxy)ethyl acetoacetate.

MaAcAc 1000 MW Oligomer (synthesis provided below) is an acetoacetoxy-functionalized reactive liquid modifier having an oligomeric molecular weight of approximately 1000.

MaAcAc 2000 MW Oligomer (synthesis provided below) is an acetoacetoxy-functionalized reactive liquid modifier having an oligomeric molecular weight of approximately 2000.

Music wire (0.005" and 0.010" in diameter) (available from Small Parts Inc. in Miramar, Fla., USA).

PARALOID EXL 2600 (available from Rohm and Haas Company in Philadelphia, Pa., USA) is a methacrylate/butadiene/styrene polymer with a core/shell architecture (core crosslinked rubber comprising of a polybutadiene-co-polystyrene-copolymer; shell: polymethacrylate) with a particle size of approximately 250 nm.

SR602 (available from Sartomer Company, Inc. in Exton, Pa., USA) is an ethoxylated (10) bisphenol A diacrylate.

t-butyl acetoacetate (available from Aldrich Chemical Company in Milwaukee, Wis., USA).

TTD (available from TCI America in Portland, Oreg., USA) is 4,7,10-trioxa-1,13-tridecane diamine.

Urethane diAcAc #1 (synthesis provided below) is an acetoacetoxy-terminated urethane reactive liquid modifier.

Urethane diAcAc #2 (synthesis provided below) is an acetoacetoxy-terminated urethane reactive liquid modifier.

VAZO-52 (available from DuPont Chemicals in Wilmington, Del., USA) is an azo free-radical initiator.

VAZO-67 or AIBN (available from DuPont Chemicals in Wilmington, Del., USA) is azoisobutyronitrile.

VDM (synthesis provided below) is 2-vinyl-4,4-dimethylazlactone.

Zeller-Gmelin KTL N16 (available from Zeller+Gmelin GmbH & Co. KG in Eislingen, Germany) is a deep-draw oil.

Z6040 (available from Alfa Aesar in Ward Hill, Mass., USA) is an adhesion promoter identified as (3-glycidyloxypropyl)trimethoxysilane.

Synthesis of 2-Vinyl-4,4-Dimethylazlactone

2-Vinyl-4,4-Dimethylazlactone (VDM) was prepared from N-acryloylmethylalanine (S. M. Heilmann and H. K. Smith II, *J. Appl. Polym. Sci.*, 24, 1551 (1979)) by the Taylor and Platt procedure (L. D. Taylor and T. E. Platt, *J. Polym. Sci. Polym. Lett.* Ed., 7, 597 (1969)) with ethyl chloroformate as the dehydrating agent. A modified workup procedure was used in which, instead of cooling the filtrate to crystallize the product, the filtrate was concentrated on a rotary evaporator, and the crude product was distilled just above room temperature at 0.5 Ton. Receiving flasks were cooled to −78° C. to collect the product. Typical distilled yields were approximately 80%.

Synthesis of Acrylamide Functionalized Reactive Liquid Modifiers

CPR-1250 Bisacrylamide (IV)

A round bottom flask was charged with 31.12 grams polycaprolactone diol followed by 6.95 grams VDM added carefully via pipette. The mixture was then placed in a heated bath at 80° C. and stirred as the polycaprolactone diol melted. When the melting was essentially complete, 0.4 grams DBU were added to the mixture by pipette. After about an hour at 80° C., approximately 80% of the VDM had reacted. After 24 hours at 80° C. the reaction was essentially complete as evidenced by $^1$H NMR.

120° C. and refluxed overnight using a vigoreaux condenser. The reaction product was then distilled under vacuum to remove the excess t-butyl acetoacetate. $^1$H NMR (in CDCl$_3$) confirms essentially pure Urethane diAcAc #1.

Urethane diAcAc #2 (AcAcXM)

50 grams t-butyl acetoacetate were added to 20 grams K-FLEX XM-311. The resultant mixture was heated to 120° C. and refluxed overnight using a vigoreaux condenser. The reaction product was then distilled under vacuum to remove the excess t-butyl acetoacetate. $^1$H NMR (in CDCl$_3$) confirms essentially pure Urethane diAcAc #2.

Synthesis of Acetoacetoxy Functionalized Polyalkene Reactive Liquid Modifiers

MaAcAc 1000 MW Oligomer (AcAc1K)

20 grams MaAcAc, 4.75 grams IOTGA, 0.051 grams VAZO 67 and 30 grams ethyl acetate were charged to a 4 oz.

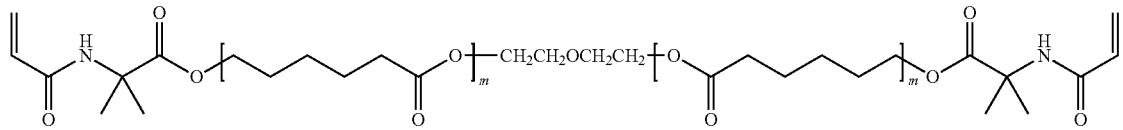

(IV)

m is 5

Synthesis of Oxalic Amide Functionalized Reactive Liquid Modifiers

DEO-400

The oxamido ester-terminated polypropylene oxide was prepared according to the below reaction scheme:

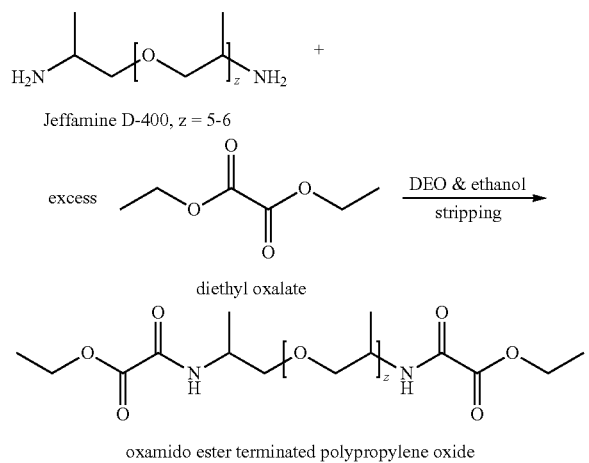

To a 2 L flask was added 730.70 grams sieve dried diethyloxalate and sufficient argon to purge the headspace. Using an addition funnel, 200.00 grams JEFFAMINE D-400 were added to the flask over the course of 90 minutes with vigorous stirring. Using a set up for distillation-argon sparge (subsurface), the temperature of the contents in the flask was slowly increased to 150° C. in order to distill out excess diethyloxalate and ethanol. The resultant product was a whisky brown, clear liquid weighing 273.2 grams and having a viscosity of 3,400 cP.

Synthesis of Acetoacetoxy Functionalized Urethane Reactive Liquid Modifiers

Urethane diAcAc #1 (AcAcUD)

35 grams t-butyl acetoacetate were added to 20 grams K-FLEX UD-320-100. The resultant mixture was heated to glass polymerization bottle. The bottle was purged with nitrogen for five minutes, sealed, and placed in a water bath maintained at 60° C. for 24 hours. The reaction mixture was then removed from the bath, and the solvent was stripped under vacuum. Peak ratio of the tail fragment protons to the backbone protons in $^1$H NMR (in CDCl$_3$) indicated approximately 4.65 repeat units per molecule, or an epoxide equivalent weight (EEW) of 270.

MaAcAc 2000 MW Oligomer (AcAc2K)

20 grams of MaAcAc, 2.32 grams IOTGA, 0.051 grams VAZO 67 and 30 grams ethyl acetate were charged to a 4 oz. glass polymerization bottle. The bottle was purged with nitrogen for five minutes, sealed, and placed in a water bath maintained at 60° C. for 24 hours. The reaction mixture was then removed from the bath, and the solvent was stripped under vacuum. Peak ratio of the tail fragment protons to the backbone protons in $^1$H NMR (in CDCl$_3$) indicated approximately 9 repeat units per molecule, or an EEW of 243.

Preparation of Epoxy Part B 307 grams of epoxy resin (DER 331) and 81 grams of the reactive diluent (EPODIL 757) were mixed together at 23° C. with stirring. The mixture was then heated in an oil bath to 80° C. with mechanical stirring. 174 grams of core-shell polymer (PARALOID EXL 2600) were added to the mixture over a period of 1 hour in small portions with stirring. After stirring an additional 30 minutes, the mixture was heated to 100° C. and held at that temperature for 4 hours. The mixture was then heated to 110° C. and stirred for another hour. The mixture was cooled to room temperature. During cooling, 12 grams of the silane coupling agent (Z6040) were stirred into the mixture.

Preparation of Epoxy Part A 99 grams of TTD (amine curative) were heated to 80° C. Then 58 grams of EPON 828 were added in small portions such that the temperature of the mixture did not rise above 100° C. 18 grams of ANCAMINE K54 were subsequently added to the mixture, and the mixture was stirred for an additional 5 minutes. The mixture was then cooled to room temperature.

Dynamic Mechanical Analysis (DMA)

Liquid reactive modifier was added to Epoxy Part B and vigorously stirred for 3-4 minutes until a uniform translucent mass was established. To that mixture Epoxy Part A was added, again with vigorous stirring for an additional 2-3 minutes until color uniformity of the yellowish mass was achieved.

The mixture was then deposited into a silicone rubber mold, which was placed atop a silicone coated PET liner. The mold was prepared earlier by stamping out parallel 5 mm wide by approximately 30 mm long rectangles and 10 mm×10 mm squares in 1.5 mm thick silicone rubber. Once spread uniformly in the mold, the mixture was covered by another silicone-coated PET liner. Then the construct was clamped between 5 mm thick plates of glass and the adhesive was cured (as described in the examples). After curing, the adhesive samples were freed from the glass, liner and mold in that order and placed into Seiko Instruments Dynamic Mechanical Analyzer.

The 5×30 mm rectangles were evaluated in tension mode using the Seiko DMS110 dynamic mechanical analyzer console and in shear mode using Seiko DMS200 dynamic mechanical console. The samples were cooled to −60° C., allowed to equilibrate at that temperature for 15 minutes and then heated at the rate of 2° C./minute to 200° C. The resulting curves of loss tangent (tan d) curve versus temperature were measured.

Cohesive Strength Method (Lap Shear Strength Testing)

Lap shear specimens were made using 4"×7"×0.063" 2024-T3 bare aluminum that had been anodized according to Boeing Aircraft Company Specification BAC-5555. The anodization voltage was 22.5 volts. The specimen was generated as described in ASTM Specification D-1002. A strip of approximately ½"×10 mils of adhesive was applied to one edge of each of the two adherends using a scraper. Three 5 mil diameter piano wires were used as spacers for bondline thickness control. The bond was closed and taped on the edge. The bond was placed between sheets of aluminum foil and pieces of cardboard. Two 14# steel plates were used to apply pressure to provide for adhesive spreading. After the adhesive had been allowed to cure (as described in the examples), the larger specimen was cut into 1" wide samples, providing a ½ square inch bonded area. Six lap shear samples were obtained from each larger specimen. The bonds were tested to failure at room temperature on a Sintech Tensile Testing machine using a crosshead displacement rate of 0.1"/min. The failure load was recorded. The lap width was measured with a vernier caliper. The quoted lap shear strengths are calculated as (2× failure load)/measured width. The average and standard deviation were calculated from the results of six tests.

T-Peel Test Method

T-peel specimens were made using 3"×8"×0.025" 2024-T3 bare aluminum that had been anodized as described above. The specimen was generated as described in ASTM D-1876. A strip of approximately 2"×5"×10 mil of adhesive was applied to both of the two adherends. 10 mil thick spacers made from brass shims were applied to the edges of the bonded area for bondline thickness control. The bond was closed and adhesive tape was applied to hold the adherends together during the cure. The adhesive bonds were placed between sheets of aluminum foil and also between pieces of cardboard. Four 14# steel plates were used to apply pressure to provide for adhesive spreading. In those cases in which the adhesive was too viscous, the T-peel specimens were placed in a hydraulic press in order to provide more force for spreading. After the adhesive had been allowed to cure (as described in the examples), the larger specimen was cut into 1" wide samples, yielding two 1" wide specimens. The bonds were tested to failure at room temperature on a Sintech Tensile Testing machine using a crosshead displacement rate of 12"/min. The initial part of the loading data was ignored. The average load was measured after about 1" was peeled. The quoted T-peel strength is the average of two peel measurements.

Example 1

Acrylate/Acrylamide-Epoxy Adhesives

Formulations

ACRYLATE1. 0.075 grams VAZO-52 initiator were pre-dissolved in 1.59 grams SR602. Then 10.94 grams Epoxy Part B were added to the solution with stirring followed by 2.47 grams Epoxy Part A with stirring.

ACRYLATE2. Part B' was made by mixing 0.218 grams BP in several drops of γ-butyrolactone. The mixture was then dissolved in 3.18 grams SR602 and stirred to dissolution. Then 12.32 grams Epoxy Part B were added to the mixture with vigorous stirring.

Part A' was prepared by mixing 0.195 grams DHEPT with several drops of γ-butyrolactone. The mixture was then dissolved in 5.56 grams of Epoxy Part A.

Part A' was then added to Part B'. To compensate for incomplete transfer of Part A', an additional 0.4 grams Epoxy Part A were added into the reaction mixture. The resultant reaction mixture was vigorously stirred.

ACRYLAMIDE1 (5%). Part B' was made by first dissolving 0.200 grams DHEPT in a couple of drops of γ-butyrolactone. The solution was then added to 1 gram CPR-1250 bisacrylamide that had been gently heated to melt (80° C.). To the resulting mixture was added 15.51 grams Epoxy Part B.

Part A' was made by first dissolving 0.2 grams BP in a couple of drops of γ-butyrolactone. The solution was then added to 4.3 grams Epoxy Part A. The amount of Epoxy Part A was sufficient to obtain transfer of approximately 3.50 grams Epoxy Part B for the adhesive sample lay up, with minimal left over in the parent container.

Part A' was then added to Part B'.

ACRYLAMIDE2 (7%). Part B' was made by mixing 0.218 grams BP in several drops of γ-butyrolactone. The solution was then dissolved in 3.18 grams CPR-1250 bisacrylamide and stirred to dissolution. Then 12.32 grams Epoxy Part B were added to the mixture with vigorous stirring.

Part A' was prepared by mixing 0.195 grams DHEPT with several drops of γ-butyrolactone. The mixture was then dissolved in 5.56 grams Epoxy Part A.

Part A' was then added to Part B'. To compensate for incomplete transfer of Part A', an additional 0.4 grams Epoxy Part A were added into the reaction mixture. The resultant reaction mixture was vigorously stirred.

EPOXYST. 1.841 grams Part A were added to 8.159 grams Part B, and the mixture was stirred vigorously for 2-3 minutes until homogeneous.

DMA

DMA was conducted on the following acrylate-epoxy adhesives.

ACRYLATE1-60. A sufficient amount of ACRYLATE1 was added to the silicone rubber mold and analyzed according to the DMA procedure described above. Curing was conducted for 1 hour at 60° C. followed by 30 minutes at 180° C. After cooling to room temperature, the cured samples were freed from the mold and analyzed. A plot of tangent delta versus temperature for ACRYLATE1-60 is shown in FIG. 1.

ACRYLATE1-100. A sufficient amount of ACRYLATE1 was added to the silicone rubber mold and analyzed according to the DMA procedure described above. Curing was conducted for 1 hour at 100° C. followed by 30 minutes at 180° C. After cooling to room temperature, the cured samples were freed from the mold and analyzed. A plot of tangent delta versus temperature for ACRYLATE1-100 is shown in FIG. 1.

ACRYLATE2-RT. A sufficient amount of ACRYLATE2 was added to the silicone rubber mold and analyzed according to the DMA procedure described above. Curing was conducted overnight at room temperature. The cured samples were freed from the mold and analyzed. A plot of tangent delta versus temperature for ACRYLATE2-RT is shown in FIG. 1.

EPOXYST. A sufficient amount of EPOXYST was added to the silicone rubber mold and analyzed according to the DMA procedure described above. Curing was conducted over night at room temperature followed by 30 minutes at 180° C. The samples were then allowed to cool to room temperature. The samples were removed from the mold and analyzed. A plot of tangent delta versus temperature for EPOXYST is shown in FIG. 1.

Strength Tests

The adhesive strength of the acrylate-epoxy and acrylamide-epoxy adhesives were determined by the lap shear and T-peel strength tests described above. All tests were conducted on etched aluminum and cured under the following conditions.

ACRYLATE1-110-180. ACRYLATE1 was cured for 30 minutes at 110° C. followed by 30 minutes at 180° C. The lap shear measurement was 3976 lb/in². The T-peel measurement was 63 lb/in-width.

ACRYLATE1-RT-180. ACRYLATE1 was cured at room temperature overnight and then placed in an oven for 30 minutes at 180° C. The lap shear measurement was 2867 lb/in². The T-peel measurement was 37 lb/in-width.

ACRYLATE1-110. ACRYLATE1 was prepared using a hot press that was preset to 110° C. and approximately 3.5 psi (1000 lbs over 2 ft² pressure). The samples were kept in the press for approximately 1 hour. The lap shear measurement was 4276 lb/in². The T-peel measurement was 51 lb/in-width.

ACRYLATE1-110-180. ACRYLATE1 was prepared using a hot press that was preset to 110° C. and approximately 3.5 psi (1000 lbs over 2 ft² pressure). The samples were kept in the press for approximately 1 hour followed by 30 minutes at 180° C. The lap shear measurement was 4152 lb/in². The T-peel measurement was 44 lb/in-width.

ACRYLAMIDE1-110-180. ACRYLAMIDE1 was cured for 30 minutes at 110° C. followed by 30 minutes at 180° C. The lap shear measurement was 3880 lb/in². The T-peel measurement was 61 lb/in-width.

ACRYLAMIDE2-110-180. ACRYLAMIDE2 was cured for 30 minutes at 110° C. followed by 30 minutes at 180° C. The lap shear measurement was 4898 lb/in². The T-peel measurement was 49 lb/in-width.

Example 2

Oxalic Amide-Epoxy Adhesives

Oxalic amide-epoxy formulations were prepared by mixing together Epoxy Part B, Epoxy Part A and DEO-400 in the amounts shown in Table 1. Specifically, DEO-400 was added to Part B and stirred for 2-3 minutes to obtain a uniform mixture. Then, Part A was added to the mixture and the mixture was stirred for an additional 2-3 minutes until uniform.

TABLE 1

| Adhesive | Wt % DEO-400 | Part B (g) | DEO-400 (g) | Part A (g) |
|---|---|---|---|---|
| DEO5.3 | 5.3% | 7.56 | 0.53 | 1.91 |
| DEO7 | 7% | 11.05 | 1.05 | 2.90 |
| DEO10.6 | 10.6% | 6.96 | 1.06 | 1.98 |
| DEO19.7 | 19.7% | 5.93 | 1.97 | 2.10 |
| DEO25.3 | 25.3% | 5.30 | 2.53 | 2.17 |

DMA

Figure 2:
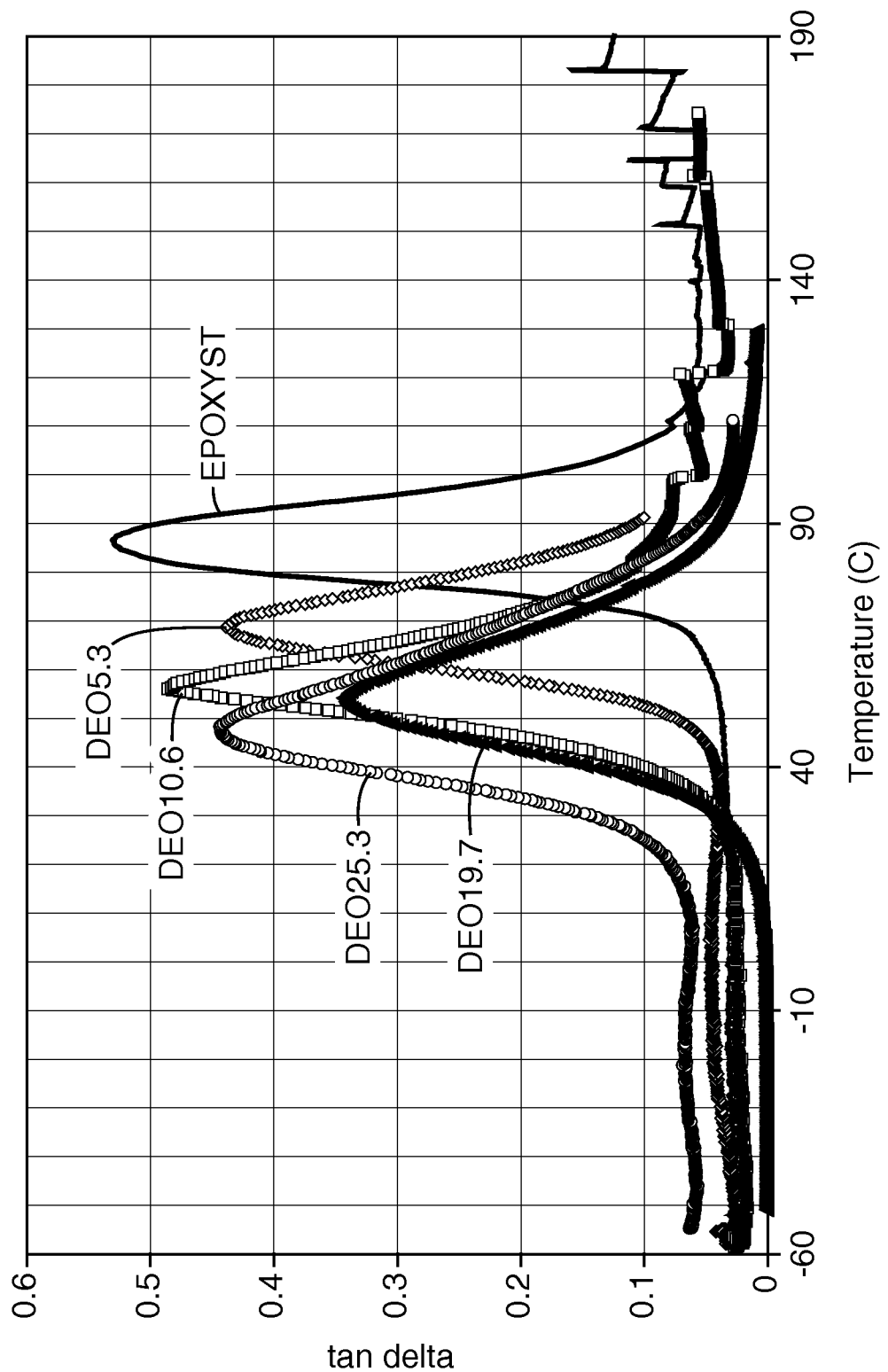
FIG. 2 is a DMA plot of tangent delta versus temperature for various oxalic amide-epoxy adhesives described in Example 2.

A sufficient amount of adhesive was added to the silicone rubber mold and analyzed according to the DMA procedure described above. Curing was conducted for 18 hours at room temperature followed by 2 hours at 80° C. After cooling to room temperature, the cured samples were freed from the mold and analyzed. DMA plots of tangent delta versus temperature for various adhesives are shown in FIG. 2.

Strength Tests

The adhesive strength of DEO7 was determined by the lap shear and T-peel strength tests described above. Both tests were conducted on etched aluminum and the adhesive was cured for 30 minutes at 110° C. followed by 30 minutes at 180° C. The lap shear measurement was 5214 lb/in². The T-peel measurement was 70 lb/in-width.

Example 3

PolyurethaneAcAc-Epoxy Adhesives

AcAcUD-epoxy formulations were prepared by mixing together Epoxy Part B, Epoxy Part A and AcAcUD in the amounts shown in Table 2. Specifically, AcAcUD was added to Part B and stirred for 2-3 minutes to obtain a uniform mixture. Then, Part A was added to the mixture and the mixture was stirred for an additional 2-3 minutes until uniform.

TABLE 2

| Adhesive | Wt % AcAcUD | Part B (g) | AcAcUD (g) | Part A (g) |
|---|---|---|---|---|
| AcAcUD5.3 | 5.3% | 7.52 | 0.53 | 1.95 |
| AcAcUD7 | 7% | 10.97 | 1.05 | 2.99 |
| AcAcUD10.6 | 10.6% | 6.88 | 1.06 | 2.06 |
| AcAcUD19.7 | 19.7% | 5.77 | 1.97 | 2.25 |
| AcAcUD25.3 | 25.3% | 5.09 | 2.53 | 2.36 |

AcAcXM-epoxy formulations were prepared by mixing together Epoxy Part B, Epoxy Part A and AcAcXM in the amounts shown in Table 3. Specifically, AcAcXM was added to Part B and stirred for 2-3 minutes to obtain a uniform mixture. Then, Part A was added to the mixture and the mixture was stirred for an additional 2-3 minutes until uniform.

TABLE 3

| Adhesive | Wt % AcAcXM | Part B (g) | AcAcXM (g) | Part A (g) |
|---|---|---|---|---|
| AcAcXM5.3 | 5.3% | 7.65 | 0.53 | 1.82 |
| AcAcXM7 | 7% | 11.24 | 1.05 | 2.72 |
| AcAcXM10.6 | 10.6% | 7.15 | 1.06 | 1.79 |
| AcAcXM19.7 | 19.7% | 6.28 | 1.97 | 1.75 |
| AcAcXM25.3 | 25.3% | 5.74 | 2.53 | 1.73 |

DMA

Figure 3:
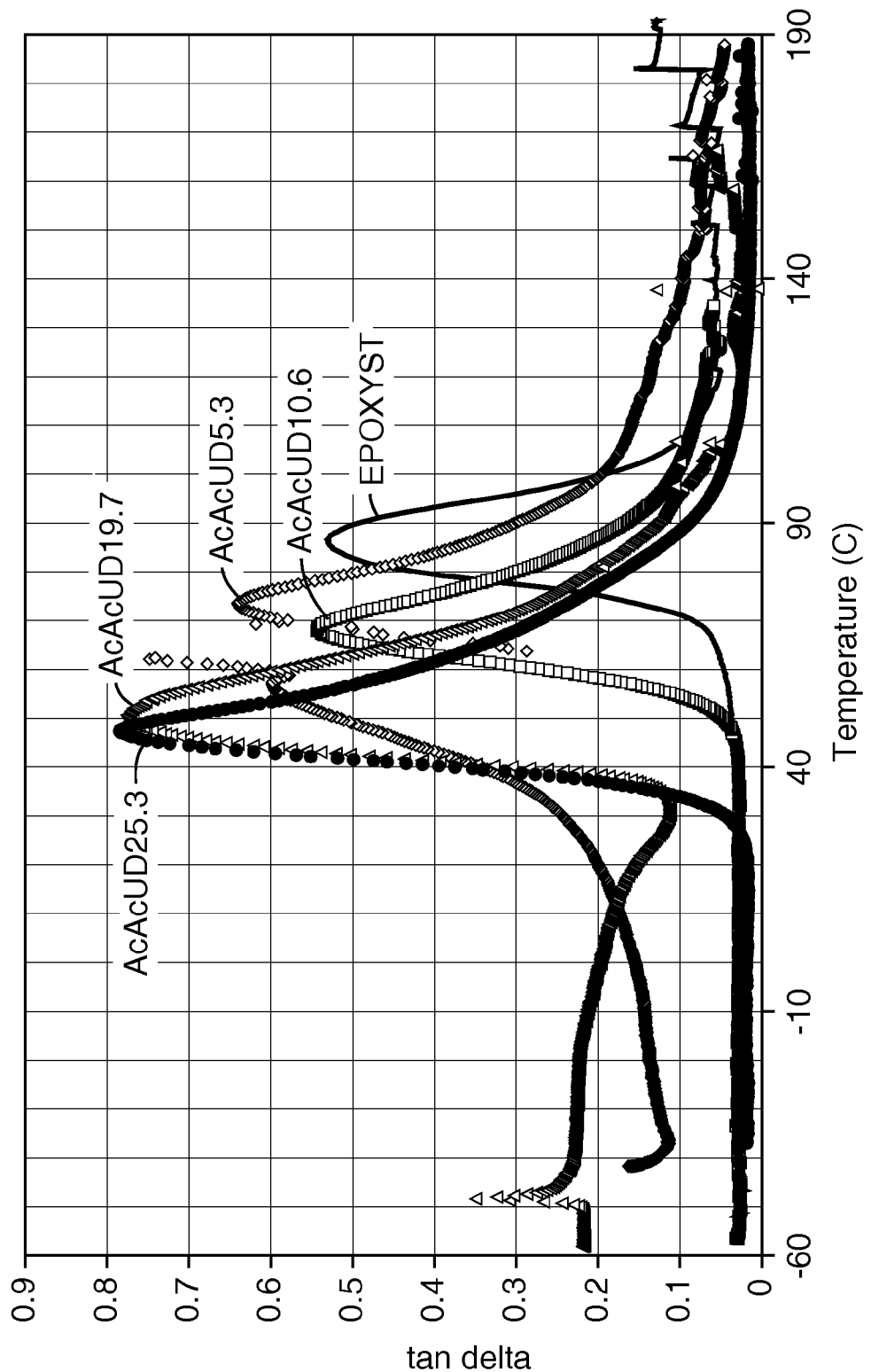
FIG. 3 is a DMA plot of tangent delta versus temperature for various AcAcUD-epoxy adhesives described in Example 3.
Figure 4:
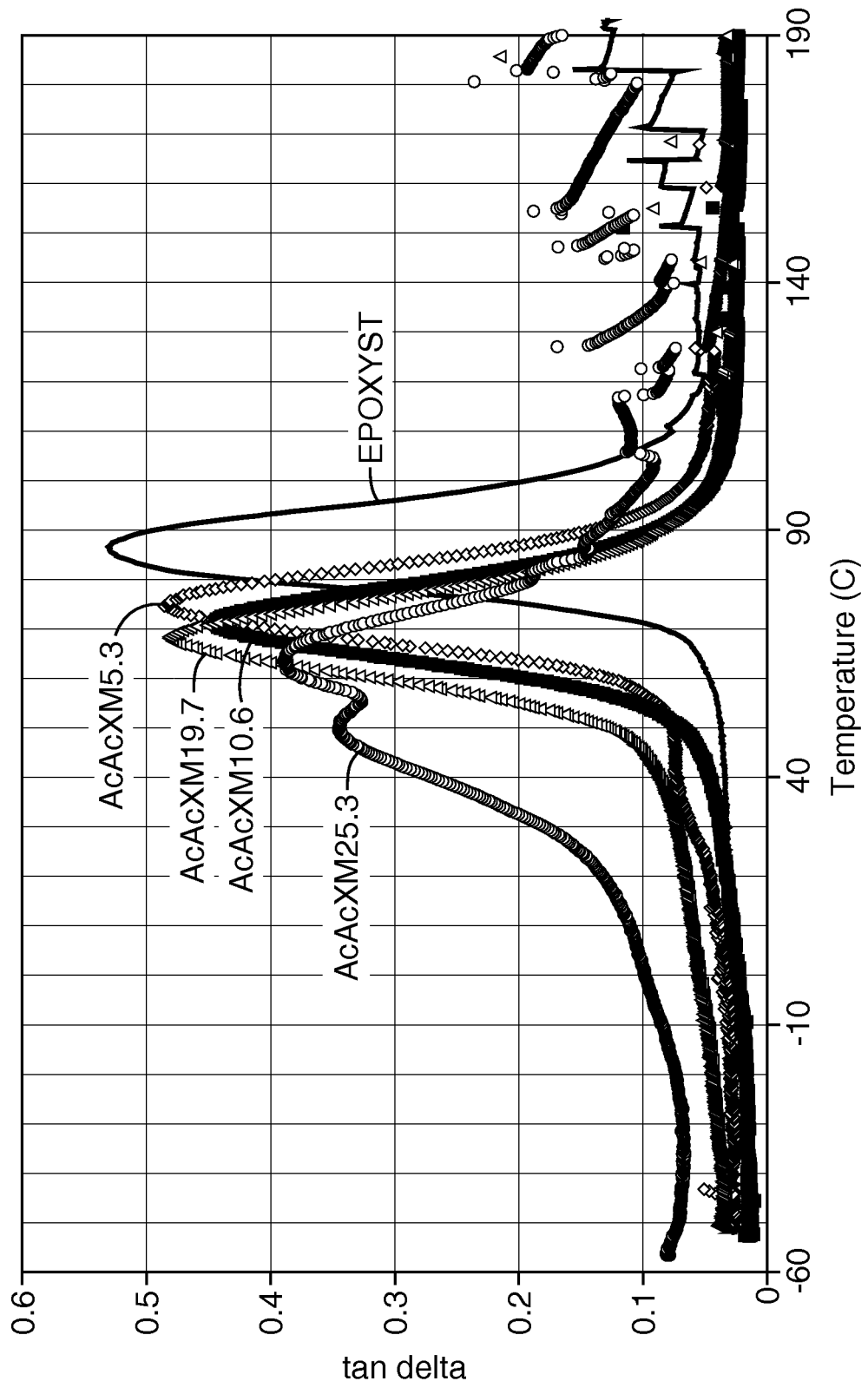
FIG. 4 is a DMA plot of tangent delta versus temperature for various AcAcXM-epoxy adhesives described in Example 3.

A sufficient amount of adhesive was added to the silicone rubber mold and analyzed according to the DMA procedure described above. Curing was conducted for 18 hours at room temperature followed by 30 minutes at 180° C. After cooling to room temperature, the cured samples were freed from the mold and analyzed. Plots of tangent delta versus temperature for various adhesives are shown in FIG. 3 (AcAcUD samples) and FIG. 4 (AcAcXM samples).

Strength Tests

The adhesive strengths of AcAcUD7 and AcAcXM7 were determined by the lap shear and T-peel strength tests described above. Both tests were conducted on etched aluminum and the adhesives were cured for 30 minutes at 110° C. followed by 30 minutes at 180° C. AcAcUD7 exhibited a lap shear strength of 4505 lb/in$^2$ and a T-peel strength of 64 lb/in-width. AcAcXM7 exhibited a lap shear strength of 5186 lb/in$^2$ and a T-peel strength of 57 lb/in-width.

Example 4

AcAcPolyalkene-Epoxy Adhesives

AcAc1K-epoxy formulations were prepared by mixing together Epoxy Part B, Epoxy Part A and AcAc1K in the amounts shown in Table 4. Specifically, AcAc1K was added to Part B and stirred for 2-3 minutes to obtain a uniform mixture. Then, Part A was added to the mixture and the mixture was stirred for an additional 2-3 minutes until uniform.

TABLE 4

| Adhesive | Wt % AcAc1K | Part B (g) | AcAc1K (g) | Part A (g) |
|---|---|---|---|---|
| AcAc1K5.3 | 5.3% | 7.54 | 0.53 | 1.93 |
| AcAc1K7 | 7% | 11.01 | 1.05 | 2.94 |
| AcAc1K10.6 | 10.6% | 6.92 | 1.06 | 2.02 |
| AcAc1K19.7 | 19.7% | 5.85 | 1.97 | 2.18 |
| AcAc1K25.3 | 25.3% | 5.20 | 2.53 | 2.27 |

AcAc2K-epoxy formulations were prepared by mixing together Epoxy Part B, Epoxy Part A and AcAc2K in the amounts shown in Table 5. Specifically, AcAc2K was added to Part B and stirred for 2-3 minutes to obtain a uniform mixture. Then, Part A was added to the mixture and the mixture was stirred for an additional 2-3 minutes until uniform.

TABLE 5

| Adhesive | Wt % AcAc2K | Part B (g) | AcAc2K (g) | Part A (g) |
|---|---|---|---|---|
| AcAc2K5.3 | 5.3% | 7.52 | 0.53 | 1.95 |
| AcAc2K7 | 7% | 10.97 | 1.05 | 2.98 |
| AcAc2K10.6 | 10.6% | 6.88 | 1.06 | 2.06 |
| AcAc2K19.7 | 19.7% | 5.77 | 1.97 | 2.26 |
| AcAc2K25.3 | 25.3% | 5.10 | 2.53 | 2.37 |

DMA

Figure 5:
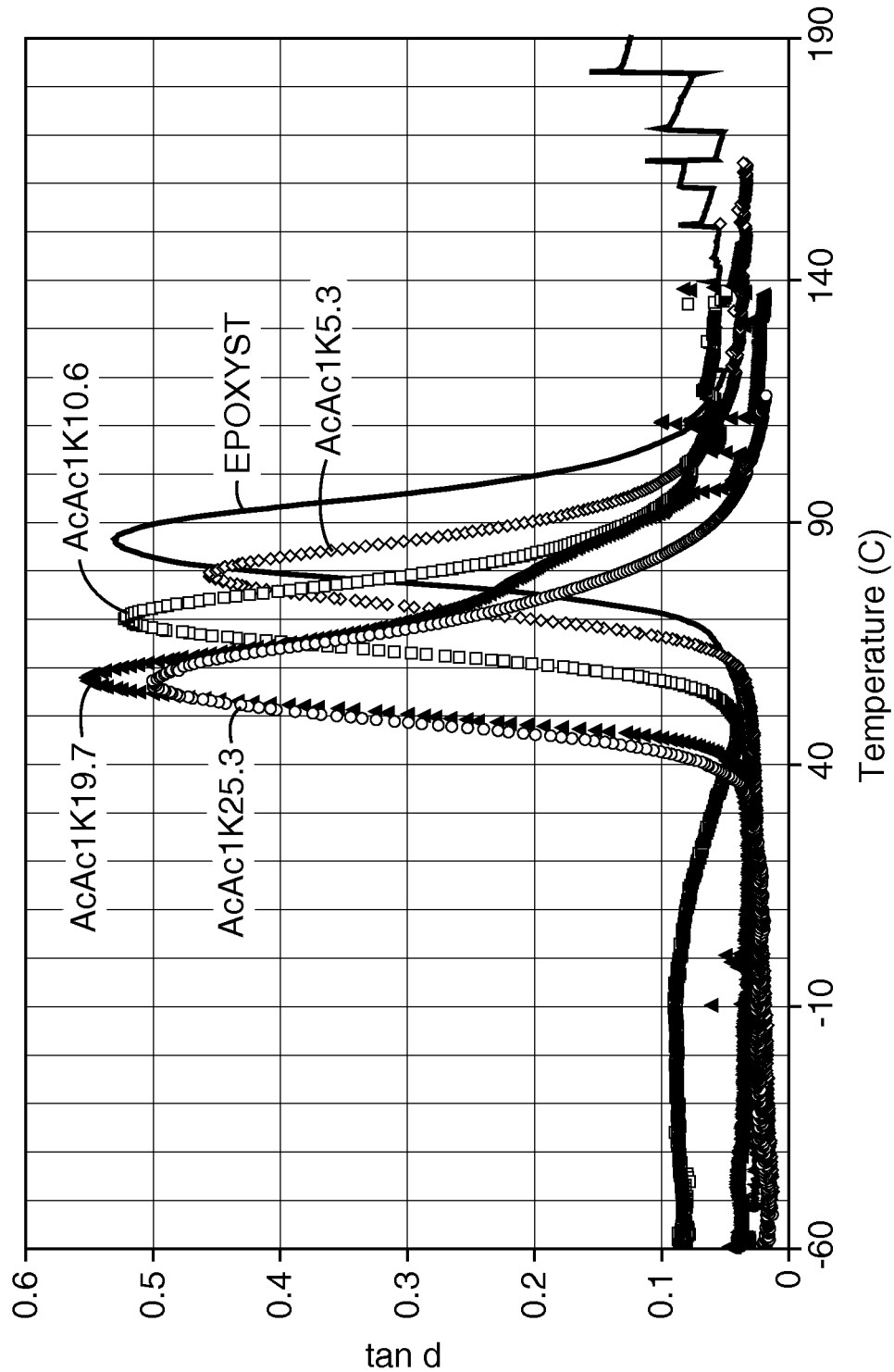
FIG. 5 is a DMA plot of tangent delta versus temperature for various AcAc1K-epoxy adhesives described in Example 4.
Figure 6:
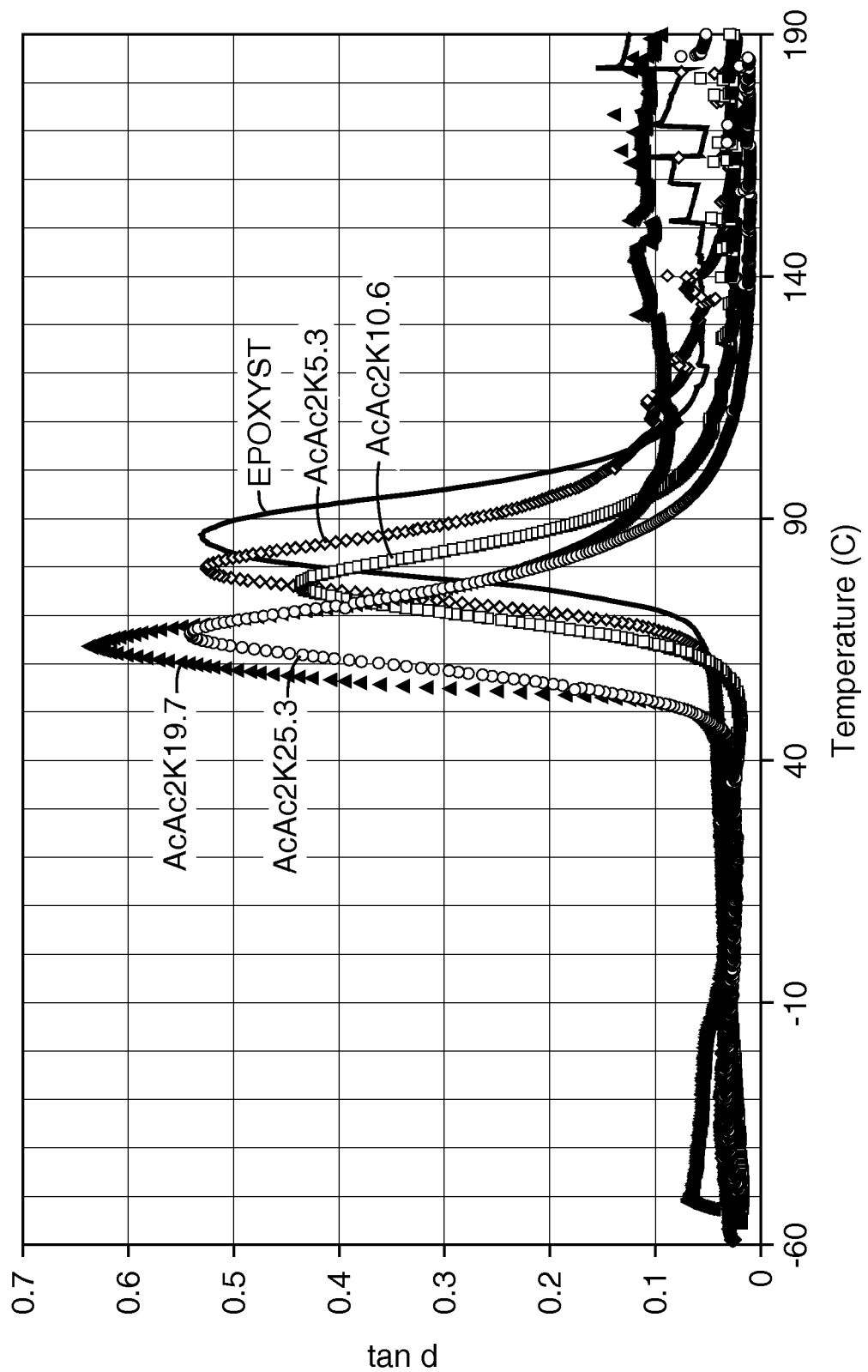
FIG. 6 is a DMA plot of tangent delta versus temperature for various AcAc2K-epoxy adhesives described in Example 4.

A sufficient amount of adhesive was added to the silicone rubber mold and analyzed according to the DMA procedure described above. Curing was conducted for 18 hours at room temperature followed by 30 minutes at 180° C. After cooling to room temperature, the cured samples were freed from the mold and analyzed. Plots of tangent delta versus temperature for various adhesives are shown in FIG. 5 (AcAc1K samples) and FIG. 6 (AcAc2K samples).

Strength Tests

The adhesive strengths of AcAc1K7 and AcAc2K7 were determined by the lap shear and T-peel strength tests described above. Both tests were conducted on etched aluminum and the adhesives were cured for 30 minutes at 110° C. followed by 30 minutes at 180° C. AcAc1K7 exhibited a lap shear strength of 4524 lb/in$^2$ and a T-peel strength of 64 lb/in-width. AcAc2K7 exhibited a lap shear strength of 3836 lb/in$^2$ and a T-peel strength of 38 lb/in-width.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Thus, the invention provides, among other things, a reactive liquid modifier for use in epoxy resin compositions. Various features and advantages of the invention are set forth in the following claims.

What is claimed is:

1. An epoxy resin composition comprising:
    a curable epoxy resin;
    an amine curing agent; and
    a reactive liquid modifier comprising a compound having the formula

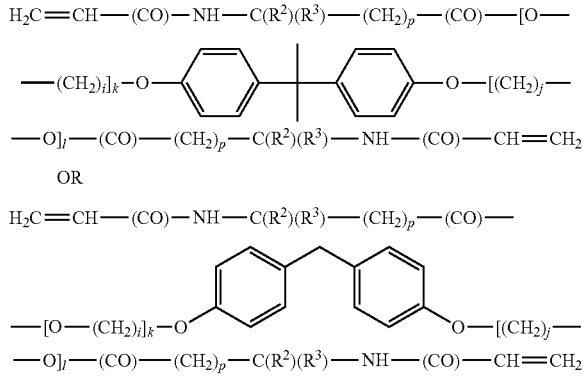

wherein
    i and j are each, independently, integer values ranging from about 1 to 10;
    k and l are each, independently, integer values of at least 1 whose combined sum ranges from about 2 to 120;
    $R^2$ and $R^3$ are each, independently, an alkyl group having from about 1 to 14 carbon atoms, a cycloalkyl group having from about 3 to 14 carbon atoms, an aryl group having from about 5 to 12 ring atoms, and arenyl group having from about 6 to 26 carbon atoms and about 0 to 3 S, N, or nonperoxidic O atoms, or $R^2$ and $R^3$ taken together with the carbon to which they are both joined form a carbocyclic ring having from about 4 to 12 carbon atoms; and
    each p is, independently, 0 or 1,
    and further wherein the compound is polymerized to form at least one of an interpenetrating polymer network and a semi-interpenetrating polymer network with the curable epoxy resin.

2. The composition of claim 1 wherein p is 0.

3. The composition of claim 1 wherein $R^2$ and $R^3$ are each a methyl group.

* * * * *

UNITED STATES PATENT AND TRADEMARK OFFICE
CERTIFICATE OF CORRECTION

PATENT NO.          : 8,637,614 B2
APPLICATION NO.     : 13/055192
DATED               : January 28, 2014
INVENTOR(S)         : Ilya Gorodisher Page 1 of 1

It is certified that error appears in the above-identified patent and that said Letters Patent is hereby corrected as shown below:

Title Page, Col. 2 Item (57) (Abstract)
Line 3, delete "actoacetoxy" and insert -- acetoacetoxy --

Title Page 2, Col 2 (Other Publications)
Line 12, delete "Modififed" and insert -- Modified --

Line 32, delete "Electroatractive" and insert -- Electroattractive --

In the Specification

Column 18
Line 36, delete "dinaphrhylmethane," and insert -- dinaphenylmethane, --

Line 41, delete "dihydroxydiphenylpropylenphenylmethane" and insert
-- dihydroxydiphenylpropylenephenylmethane, --

Column 24
Line 38, delete "boid" and insert -- void --

Column 27
Line 67, delete "cyclohexandimethanoldiglycidylether." and insert
-- cyclohexanedimethanoldiglycidylether. --

Column 28
Line 9, delete "Hunstman" and insert -- Huntsman --

Column 29
Line 1, delete "Ton." and insert -- Torr. --

Signed and Sealed this
Twenty-fourth Day of June, 2014

Michelle K. Lee
*Deputy Director of the United States Patent and Trademark Office*